United States Patent
Peterson et al.

(10) Patent No.: US 11,129,689 B2
(45) Date of Patent: Sep. 28, 2021

(54) IMPLANT HOLDER

(71) Applicant: Medos International Sarl, Le Locle (CH)

(72) Inventors: Joseph Peterson, South Dartmouth, MA (US); Frank Spratt, Middleboro, MA (US); Kristina Carlson, Boston, MA (US); Paul Maguire, Hope Valley, RI (US); Eric Biester, Providence, RI (US); Rick Fournier, New Bedford, MA (US)

(73) Assignee: Medos International Sarl, Le Locle (CH)

( * ) Notice: Subject to any disclaimer, the term of this patent is extended or adjusted under 35 U.S.C. 154(b) by 21 days.

(21) Appl. No.: 16/697,726

(22) Filed: Nov. 27, 2019

(65) Prior Publication Data
US 2021/0153968 A1 May 27, 2021

(51) Int. Cl.
*A61B 50/30* (2016.01)
*A61B 17/88* (2006.01)
*A61B 17/84* (2006.01)
*A61B 17/70* (2006.01)
*A61B 17/56* (2006.01)

(52) U.S. Cl.
CPC .......... *A61B 50/30* (2016.02); *A61B 17/7032* (2013.01); *A61B 17/84* (2013.01); *A61B 17/8872* (2013.01); *A61B 2017/564* (2013.01)

(58) Field of Classification Search
CPC ....... A61B 17/84; A61B 17/86; A61B 17/865; A61B 17/88; A61B 17/8872; A61B 50/30
See application file for complete search history.

(56) References Cited

U.S. PATENT DOCUMENTS

| 4,856,648 A * | 8/1989 | Krueger ............... A61C 8/0087 206/63.5 |
| 5,062,800 A | 11/1991 | Niznick |
| 5,332,443 A | 7/1994 | Chew et al. |
| 5,437,550 A | 8/1995 | Beaty et al. |

(Continued)

FOREIGN PATENT DOCUMENTS

| DE | 10146905 A1 | 7/2003 |
| WO | 00/02496 A1 | 1/2000 |

(Continued)

OTHER PUBLICATIONS

International Search Report and Written Opinion received for PCT International Application No. PCT/FR2011/050943, dated Oct. 19, 2011, 13 pages.

*Primary Examiner* — Matthew J Lawson
(74) *Attorney, Agent, or Firm* — Mintz Levin Cohn Ferris Glovsky and Popeo, P.C.

(57) ABSTRACT

Various implant holding systems are provided herein that include an outer tube, an inner tube, and a holder. The implant holding systems can be designed to hold various implants, such as bone anchors used in spinal operations. For example, one embodiment of an implant holding system can have an outer tube, an inner tube that can be disposed within the outer tube, and an implant holder that can be disposed within the inner tube. An individual bone anchor that has various configurations and sizes can be disposed within the holder, and the holder can engage the bone anchor to assist in maintaining an orientation of the bone anchor relative to the holder.

19 Claims, 27 Drawing Sheets

(56) References Cited

U.S. PATENT DOCUMENTS

| | | |
|---|---|---|
| 5,538,428 A | 7/1996 | Staubli |
| 5,558,230 A | 9/1996 | Fischer et al. |
| 5,622,500 A | 4/1997 | Niznick |
| 5,692,904 A | 12/1997 | Beaty et al. |
| 6,203,323 B1 | 3/2001 | Beaty et al. |
| 6,217,332 B1 | 4/2001 | Kumar |
| 6,247,932 B1 | 6/2001 | Sutter |
| 6,287,117 B1 | 9/2001 | Niznick |
| 7,490,723 B2 | 2/2009 | Levisman |
| 7,650,991 B2 | 1/2010 | Hester et al. |
| 7,854,316 B2 | 12/2010 | Park et al. |
| 7,921,991 B2 * | 4/2011 | Sato ............... A61C 8/0087 206/63.5 |
| 8,083,054 B2 | 12/2011 | Nihei et al. |
| 8,087,325 B2 | 1/2012 | Neubardt |
| 8,292,174 B2 | 10/2012 | Bagozzi et al. |
| 8,372,419 B2 | 2/2013 | Hellerbrand et al. |
| 8,662,299 B2 | 3/2014 | Pratt et al. |
| 9,694,968 B2 | 7/2017 | Roesler |
| 9,839,459 B2 | 12/2017 | Derouet et al. |
| 9,872,754 B2 | 1/2018 | Tuechsen et al. |
| 9,975,679 B2 | 5/2018 | Hulliger |
| 10,398,523 B2 * | 9/2019 | Roesler .............. B65D 81/05 |
| 10,939,927 B2 * | 3/2021 | Garcia ............... A61B 17/3403 |
| 2003/0221977 A1 | 12/2003 | Kumar et al. |
| 2004/0256267 A1 | 12/2004 | Roger |
| 2005/0098460 A1 | 5/2005 | Smith et al. |
| 2006/0243616 A1 | 11/2006 | Caron |
| 2007/0119871 A1 | 5/2007 | Garcia |
| 2007/0209957 A1 | 9/2007 | Glenn et al. |
| 2009/0266728 A1 | 10/2009 | Turner et al. |
| 2014/0174971 A1 | 6/2014 | Lindner et al. |
| 2016/0228188 A1 | 8/2016 | Sweeney |
| 2016/0249995 A1 | 9/2016 | Ritchey et al. |
| 2016/0287293 A1 | 10/2016 | Karas et al. |
| 2017/0095308 A1 | 4/2017 | Roesler et al. |
| 2017/0340371 A1 | 11/2017 | Wahl et al. |
| 2019/0150989 A1 | 5/2019 | Biester et al. |
| 2019/0321123 A1 * | 10/2019 | Richart .............. B65D 77/0493 |
| 2021/0113248 A1 * | 4/2021 | D'Andrea .............. A61B 50/30 |

FOREIGN PATENT DOCUMENTS

| | | |
|---|---|---|
| WO | 2009/024189 A2 | 2/2009 |
| WO | 2011/135246 A2 | 11/2011 |
| WO | 2017/181081 A2 | 10/2017 |
| WO | 2018/009401 A1 | 1/2018 |
| WO | 2018/081339 A1 | 5/2018 |

* cited by examiner

FIG 28   FIG 29   FIG 30   FIG 31
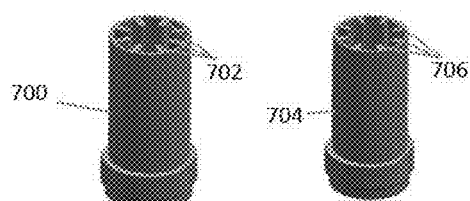
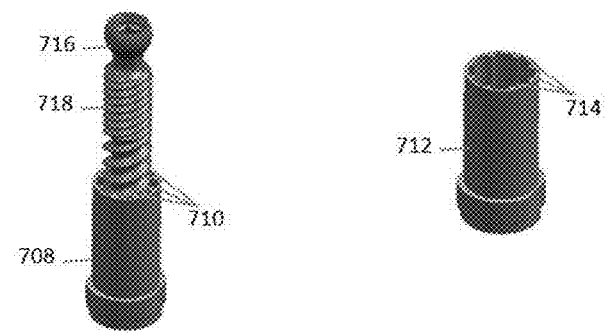
FIG 32   FIG 33   FIG 34
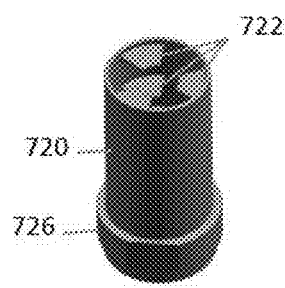
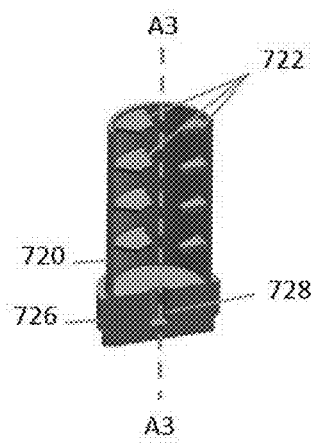
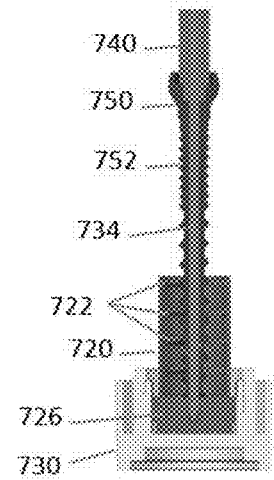

FIG 44  FIG 45  FIG 46
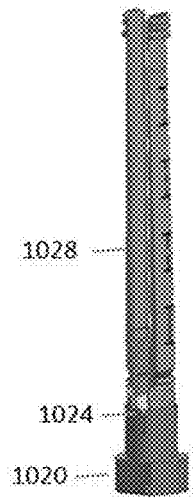
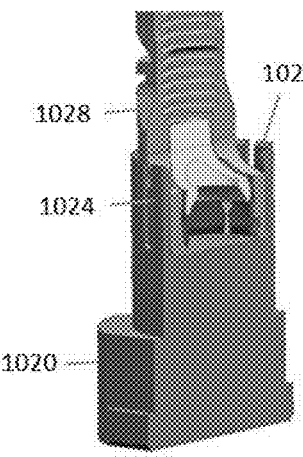
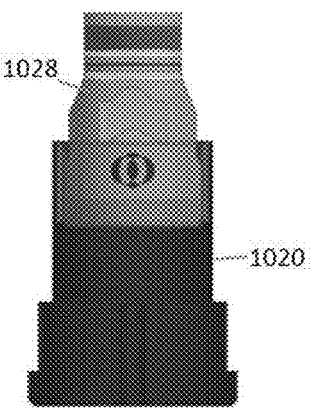
FIG 47  FIG 48  FIG 49
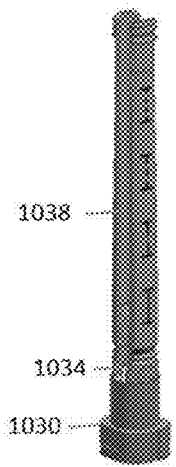
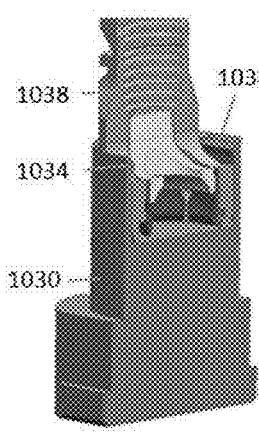
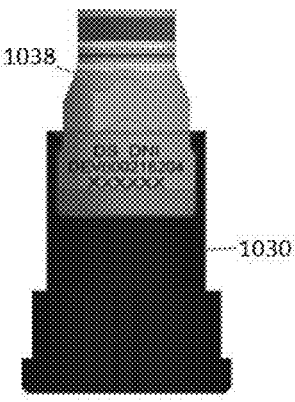

FIG 50    FIG 51    FIG 52
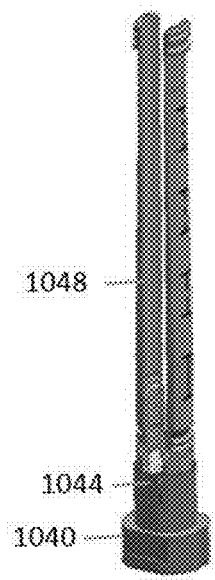 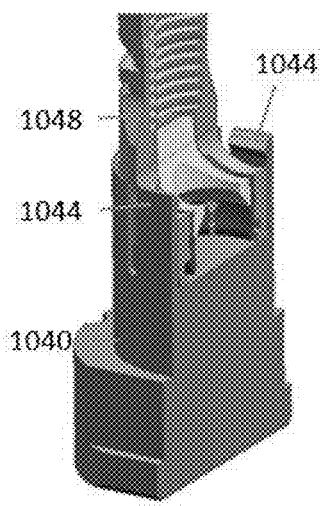 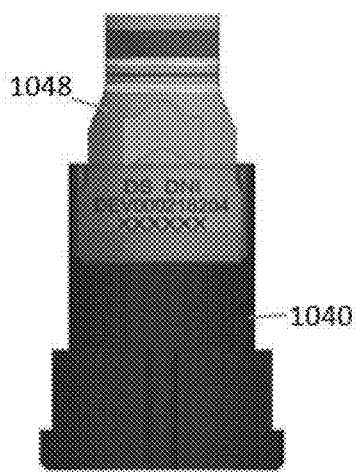
FIG 53    FIG 54
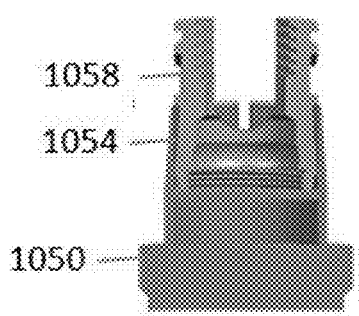 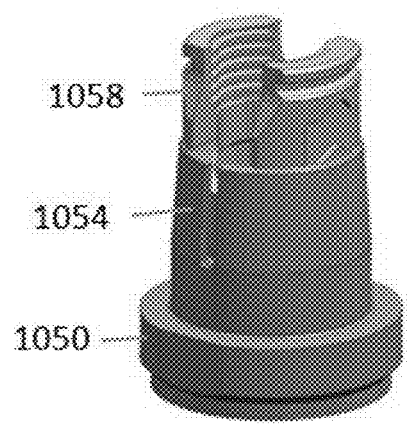

IMPLANT HOLDER

FIELD

The present disclosure relates generally to implant holders.

BACKGROUND

During various surgical operations, it is necessary to maintain a surgically sterile environment. As such, preparing for operations that require multiple tools and implants, such as spinal operations in which a plurality of bone anchors may be used, can be very time consuming because a user is required to sterilize a number of different implants. Additionally, many bone anchors are provided to users on a large tray with numerous different sizes and configurations. A user is required to sterilize the entire tray even if an operation only requires a small number of the bone anchors on the tray, and a user must pay for, maintain, and ensure proper training is provided for any implant sterilization equipment.

Accordingly, there remains a need for improved implant holders.

SUMMARY

In general, individual implant holders and methods for using the same are provided.

In one embodiment, an implant holding system is provided that has an outer tube, an inner tube, a bone anchor, and a holder. The outer tube has a sealed first outer end and an open second outer end, and the outer tube has a removable outer cap that selectively seals the second outer end. The inner tube is disposed within the outer tube, and the inner tube has a sealed first inner end that engages the outer cap of the outer tube. The inner tube has an open second inner end and a removable inner cap that is configured to selectively seal the second inner end. The bone anchor has a driver head and a threaded shaft that extends distally from the driver head. The holder is disposed within the inner tube and has a longitudinal axis. The holder has a receiving head that receives the driver head of the bone anchor and a collar that extends distally from the receiving head. The collar engages at least part of the threaded shaft of the bone anchor to maintain the orientation of the threaded shaft of the bone anchor relative to the longitudinal axis of the holder when the bone anchor is received therein.

The system can have numerous variations. For example, the receiving head can be configured to engage the driver head of the bone anchor to prevent axial rotation about the longitudinal axis of the holder, and the receiving head can have a lumen extending distally through the receiving head and the collar such that the threaded shaft of the bone anchor can pass therethrough. In another example, the holder can include a break-off tab removably disposed at an end opposite the receiving head, and the break-off tab is configured to be removed to change a length of the holder along the longitudinal axis of the holder. In some examples, the holder can have at least two bowed, deformable legs that are configured to maintain a position of the holder within the inner tube through a frictional engagement between each of the legs and an inner surface of the inner tube. In another example, the holder can have an alignment panel disposed along a distal portion thereof, and the alignment panel can be configured to engage an inner surface of the inner tube to resist axial rotation of the holder about the longitudinal axis of the holder. The alignment panel can also have a non-circular cross section at a point along the longitudinal axis of the holder. In still another example, the holder, the outer tube, and the inner tube can allow visualization of the orientation of the bone anchor when the bone anchor is received in the holder. In one example, the outer tube, the inner tube, and the holder can be coaxial with each other along the longitudinal axis of the holder when the holder is disposed within the inner tube and the inner tube is disposed within the outer tube.

In another embodiment, an implant holding system is provided that has an outer tube, an inner tube, a bone anchor, and a holder. The outer tube has a sealed first outer end and an open second outer end, and the outer tube has a removable outer cap that selectively seals the second outer end. The inner tube is disposed within the outer tube, and the inner tube has a sealed first inner end that engages the outer cap of the outer tube. The inner tube has an open second inner end and a removable inner cap that selectively seals the second inner end. The bone anchor has a driver head. The holder is disposed within the inner tube, and the holder has a longitudinal axis that extends between a first holder end that engages the inner cap of the inner tube and an open second holder end. A lumen extends at least partially through the holder from the second holder end towards the first holder end, and the lumen receives at least part of the bone anchor therein. A plurality of alignment members extend at least partially into the lumen, and the plurality of alignment members engage the bone anchor to maintain an orientation of the bone anchor relative to the longitudinal axis of the holder when the bone anchor is received in the lumen.

The system can have numerous variations. For example, each of the plurality of alignment members can be one of a longitudinal rectangular protrusion, a perpendicular protrusion, a bowed arm, a curved arm, a spiraled arm, and a flexible arm such that a plurality of bone anchors of different lengths and diameters can be receivable in the lumen. In another example, the holder can have one or more break-off portions extending from the open second holder end toward the first holder end that can be removed to change a length of the holder along the longitudinal axis of the holder. In some examples, the bone anchor can have a threaded shaft extending distally from the driver head, and the plurality of alignment members can be arranged extending radially into the lumen to correspond with threads extending radially outward from the threaded shaft. In one example, the holder can maintain a rotational position with the inner cap of the inner tube relative to the longitudinal axis of the holder when the holder is engaged thereto. The first holder end can also have a non-circular cross section at a point along the longitudinal axis of the holder. In another example, the holder, the outer tube, and the inner tube can allow visualization of the orientation of the bone anchor when the bone anchor is received in the holder. In one example, the outer tube, the inner tube, and the holder can be coaxial with each other along the longitudinal axis of the holder when the holder is disposed within the inner tube and the inner tube is disposed within the outer tube.

In another aspect, a surgical method is provide that includes removing a sealed cover from an outer tube while the outer tube houses an inner tube and an implant holder is disposed within the inner tube. A threaded shaft of a bone anchor is held in a first orientation within the implant holder relative to a longitudinal axis of the implant holder through engagement with a receiving head and a collar of the implant holder, and an interior of the outer tube, the inner tube, the implant holder, and the bone anchor are sterile. The method also includes passing the inner tube into a sterile field without contaminating an exterior surface of the inner tube and removing a cover from the inner tube within the sterile field. The method further includes retrieving the bone anchor from the implant holder in the inner tube within the sterile field such that the threaded shaft of the bone anchor has remained in the first orientation during retrieval through engagement with the receiving head and the collar of the implant holder.

The method can have numerous variations. For example, the method can further include visually inspecting an orientation of the bone anchor through the outer tube, the inner tube, and the implant holder during removing the sealed cover from the outer tube. In another example, a driver head of the bone anchor can engage a proximal end of the threaded shaft, and the driver head and the threaded shaft of the bone anchor can be maintained in the first orientation during removing the sealed cover from the outer tube, passing the inner tube into the sterile field, and removing the cover from the inner tube. In still another example, the implant holder can hold a plurality of bone anchors of various lengths and diameters in the first orientation.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

This invention will be more fully understood from the following detailed description taken in conjunction with the accompanying drawings, in which:

FIG. 28 is a perspective view of another embodiment of an implant holder;

FIG. 29 is a perspective view of another embodiment of an implant holder;

FIG. 30 is a perspective view of another embodiment of an implant holder with another embodiment of a bone anchor;

FIG. 31 is a perspective view of another embodiment of an implant holder;

FIG. 32 is a perspective view of another embodiment of an implant holder;

FIG. 33 is a cross-sectional side view of the implant holder of FIG. 32;

FIG. 34 is a cross-sectional side view of the implant holder of FIG. 32 with a tool and a stylet;

FIG. 44 is a perspective view of another embodiment of an implant holder;

FIG. 45 is a cross-sectional side view of the holder of FIG. 44;

FIG. 46 is a partially transparent side view of the holder of FIG. 44;

FIG. 47 is a perspective view of another embodiment of an implant holder;

FIG. 48 is a cross-sectional side view of the holder of FIG. 47;

FIG. 49 is a partially transparent side view of the holder of FIG. 47;

FIG. 50 is a perspective view of another embodiment of an implant holder;

FIG. 51 is a cross-sectional side view of the holder of FIG. 50;

FIG. 52 is a partially transparent side view of the holder of FIG. 50;

FIG. 53 is a cross-sectional side view of another embodiment of an implant holder;

FIG. 54 is a perspective view of the holder of FIG. 53;

DETAILED DESCRIPTION

Figure 1:
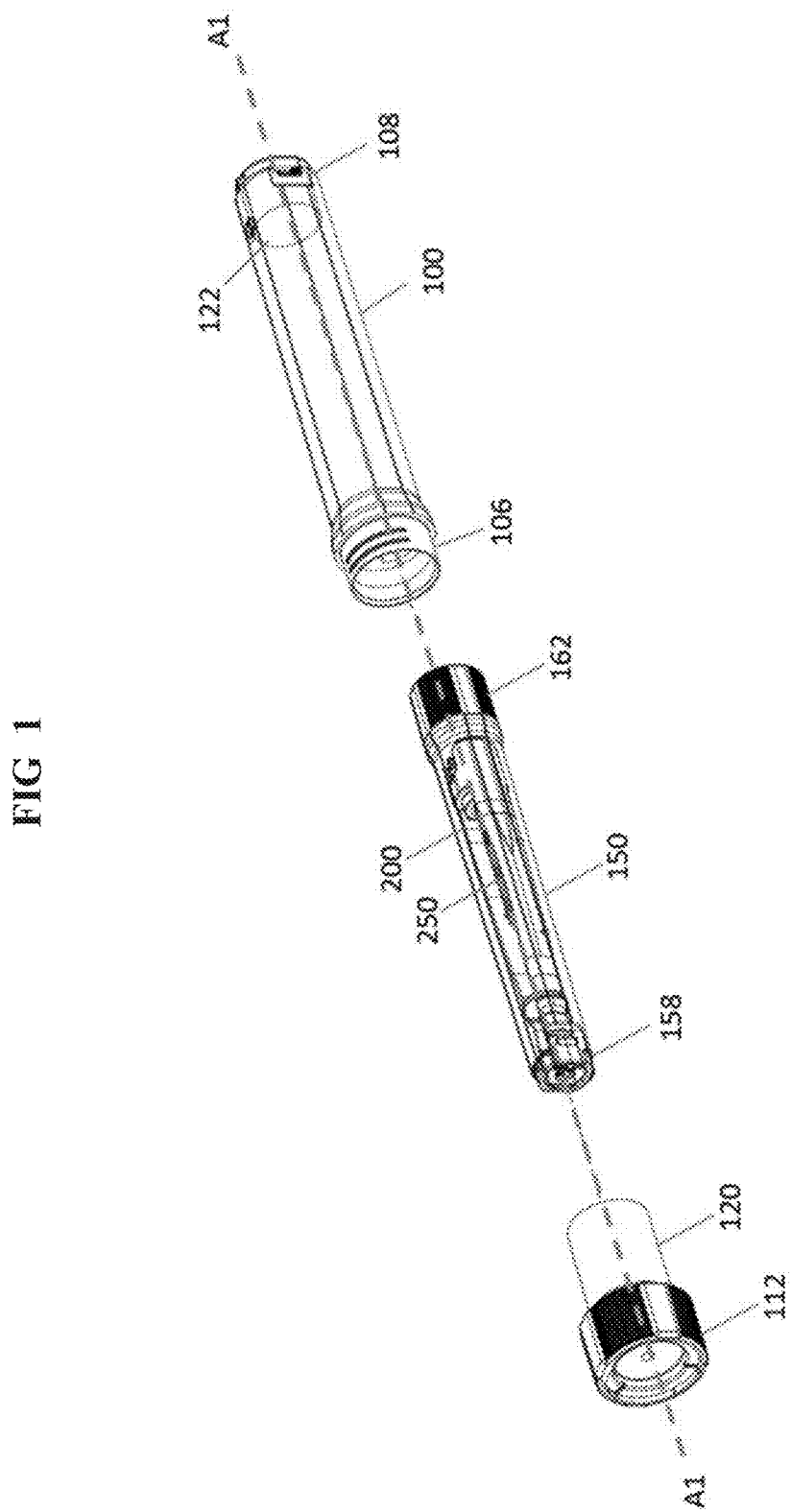
FIG. 1 is a perspective view of one embodiment of an implant holder and one embodiment of a bone anchor disposed within one embodiment of an inner tube that is aligned to be disposed within one embodiment of an outer tube.
Figure 2A:
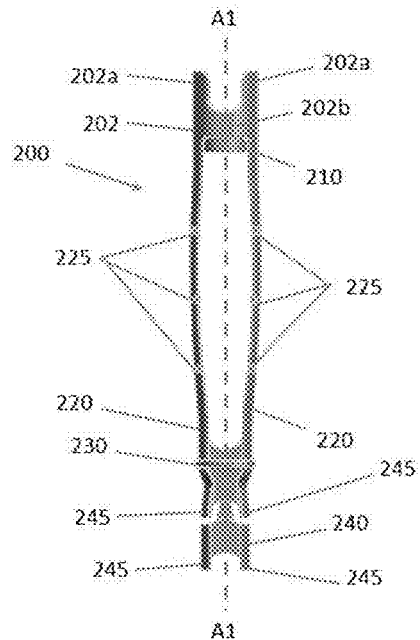
FIG. 2A is a side view of the implant holder of FIG. 1.
Figure 2B:
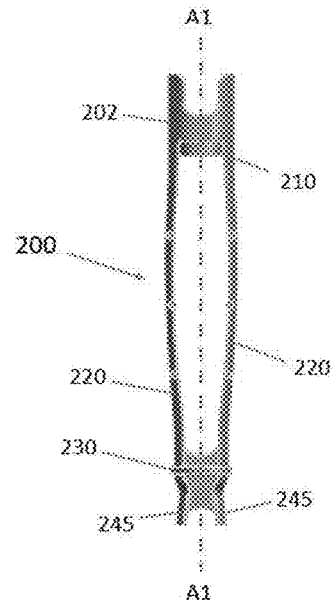
FIG. 2B is a side view of the implant holder of FIG. 1 with a break-off tab removed.
Figure 3:
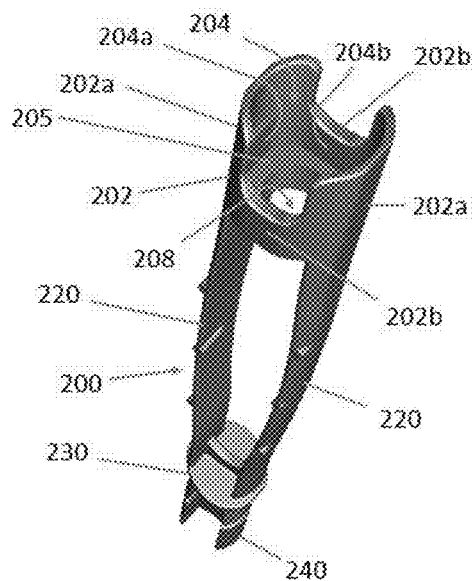
FIG. 3 is a perspective view of the implant holder of FIG. 1.
Figure 4:
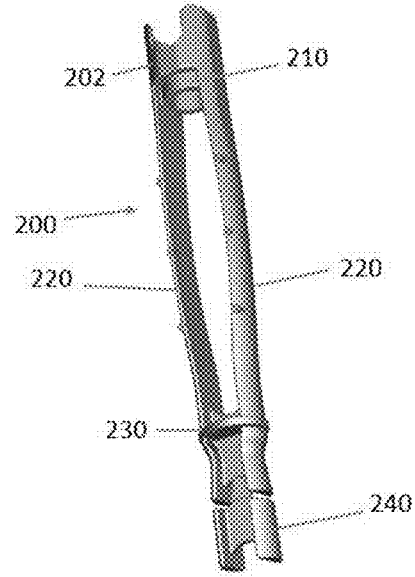
FIG. 4 is a perspective view of the implant holder of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Like reference symbols in the various drawings indicate like elements.

The present disclosure generally relates to implant holders. When various individual implants are transported, it can be helpful to maintain a general orientation of an implant to prevent the implant from being damaged during transportation and to minimize any difficulty in removing the implant from its transportation container during deployment. Additionally, it can be beneficial to sterilize and package individual implants in individual transportation containers so that, upon deployment, a user is not required to sterilize the implant and is not required to handle and potentially contaminate more than one implant at a time.

As such, various implant holding systems are provided herein that include an outer tube, an inner tube, and a holder. The implant holding systems can be designed to accommodate various implants of different types and sizes, such as bone anchors used in spinal operations, and the holder can engage a bone anchor disposed therein to assist in maintaining an orientation of the bone anchor relative to the holder. That is, the holder engages a bone anchor and is maintained within an inner tube in a sterile condition, the inner tube, in turn, is maintained within an outer tube, which need not be sterile. Ideally, a single holding system has the versatility to handle bone anchors of any size that are likely to be used.

Additionally, one or more of the bone anchor, the holder, the inner tube, and/or the outer tube can be sterilized during assembly packaging, and maintained in a sterile state until the bone anchor is to be deployed. Typically, the bone anchor, the holder, and the inner tube are sterilized before placement within the outer tube. This ensures that each bone anchor is sterilized and maintained within its own sterile enclosure, making it possible to use as many bone anchors of different types and sizes during a surgical procedure without compromising the sterility of any bone anchors that are not sued during the procedure.

FIGS. 1-24 illustrate one embodiment of an implant holding system that has an outer tube 100, an inner tube 150, and a holder 200, as collectively illustrated in FIG. 1. The holder 200 receives a bone anchor 250 therein so that an orientation of the bone anchor 250 is maintained relative to the holder 200 during movement and transport of the system. As discussed further below, the holder 200 can be placed in the inner tube 150 and can maintain a position within the inner tube 150. The inner tube 150 can be placed in the outer tube 100, and the inner tube 150 can maintain its position within the outer tube 100. As such, an orientation of the bone anchor 250 can be maintained within the holder 200 and tubes 100, 150 when it is transported, for example when being moved from a manufacturing or distribution facility to an operating environment in which the bone anchor 250 will be deployed.

As illustrated in FIGS. 2A-4, the holder 200 has a receiving head 202, a collar 210, deformable legs 220, an alignment plate 230, and a break-off tab 240. The receiving head 202 is on a proximal end of the holder, and the collar 210 and the deformable legs 220 extend distally from the receiving head 202 along a longitudinal axis A1 of the holder 200. The deformable legs 220 extend distally on either side of the collar 210, and the legs 220 terminate in the alignment plate 230 that is formed at a distal end of the legs 220. The break-off tab 240 is disposed at a distal end of the holder 200.

Figure 5:
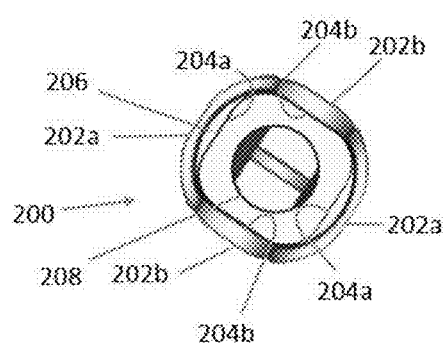
FIG. 5 is a top-down view of the implant holder of FIG. 1.
Figure 6:
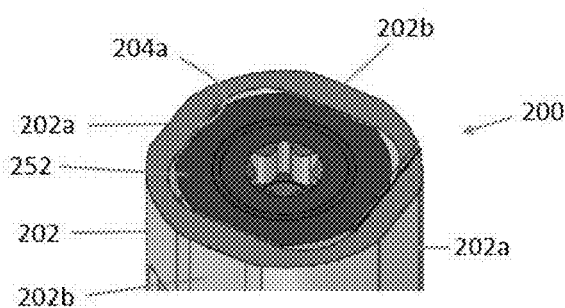
FIG. 6 is a perspective view of a top of the implant holder of FIG. 1 with one embodiment of a bone anchor.

The receiving head 202 receives a driver head 252 of the bone anchor 250 in a cavity 204 formed therein and it maintains an orientation of the driver head 252 of the bone anchor 250. The receiving head 202 has two raised flat sides 202a and two lower flat sides 202b that define the cavity 204, as illustrated in FIGS. 5 and 6. The flat sides 202a, 202b contact corresponding flat inward-facing surfaces in the inner tube 150 when the holder is disposed within the inner tube 150 to assist in preventing rotation of the holder independent of inner tube 150. The cavity 204 additionally has flat inward-facing surfaces 204a, 204b. As such, as illustrated in FIG. 6 showing a cross-section of the driver head 252 in the receiving head 202, the flat surfaces 204a, 204b can engage corresponding flat outward-facing surfaces of the driver head 252 to assist in preventing rotation of the driver head 252 independent of the holder 200.

Additionally, the receiving head 202 allows one to visualize or observe an orientation of the driver head 252 because the raised sides 202a and lower sides 202b form an approximately U-shaped profile when viewed from a side of the holder 200. The cavity 204 has a distal or lower surface 205 that engages a lower surface of the driver head 252 of the bone anchor 250, and the receiving head 202 has an opening or lumen 208 through which a threaded shaft 254 of the bone anchor 250 can extend distally along the axis A1.

In some embodiments, small gaps can be designed between the sides of the bone anchor 250, the receiving head 202, and the inner tube 150 to allow for easier insertion and removal of the holder 200 and the bone anchor 250 while still maintaining a fixed orientation. As illustrated in FIG. 5, ledges 206 and other surface features can also be formed within the cavity 204 to assist in engaging driver heads of various sizes and configurations, which can vary based on intended use(s) of various bone anchors.

While the receiving head 202 maintains an orientation of the driver head 202, the collar maintains an orientation of the threaded shaft 254 of the bone anchor 250 relative to the axis A1. As illustrated in FIGS. 2A-8G, the collar 210 extends distally from the receiving head 202, and the lumen 208 extends through the collar 210 along the axis A1. The collar 210 thus engages at least part of the threaded shaft 254 when the threaded shaft 254 extends through the lumen 208, thereby maintaining the orientation or angulation of the threaded shaft 254 in the holder 200. While the collar 210 has a circular or annular cross section, a variety of different cross-sectional shapes can be used, such as a hexagon, an octagon, etc.

Figure 9:
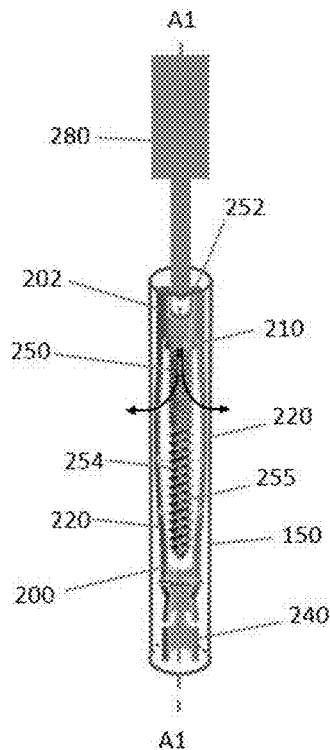
FIG. 9 is a partially transparent side view of the implant holder inserted into the inner tube of FIG. 1 with a tool and the bone anchor of FIG. 1.

Additionally, the collar 210 allows one to visualize and observe an orientation of the threaded shaft 254 during movement of the holder 200. The collar 210 extends only partially along the longitudinal axis A1 of the holder 200 so that at least a distal-most portion 255 of the threaded shaft 254 protrudes beyond the collar 210, as illustrated in FIG. 9. For example, the collar 210 can extend between approximately 5% and approximately 75% along a length of the threaded shaft 254, and more preferably between approximately 5% and approximately 35% along the length of the threaded shaft 254.

Thus, as illustrated in FIGS. 9-12, the cavity 204, the lumen 208, and the collar 210 can be sized to accept bone anchors with driver heads and threaded shafts of a variety of different sizes. For example, FIGS. 9-12 illustrate common bone anchors 250, 250b, 250c, 250d with driver heads 252, 252b, 252c, 252d and threaded shafts 254, 254b, 254c, 254d of various sizes, lengths, dimensions, configurations, etc. While several embodiments of bone anchors are illustrated, numerous types of bone anchors can be received into the holder 200, such as various polyaxial and/or modular screws detailed in US Patent App. No. 2019/0150989 of Biester et al., entitled "Bone Anchor Assemblies and Related Instrumentation," filed on Nov. 7, 2018, which is incorporated herein by reference in its entirety. Additionally, various fixed bone screws can be received in the holder 200 that have threaded shafts and driver heads in a fixed orientation with each other, as well as one or more individual components of a modular screw, such as only a threaded shaft.

Extending distally from the receiving head 202 and around the collar 210, the two legs 220 assist in maintaining an orientation of the holder 200 within the inner tube 150. The two legs 220 are deformable and bow radially outward relative to the axis A1. As such, each leg at its widest point contacts an inward-facing surface of the inner tube 150, and the holder 200 is coaxial with the inner tube 150. During placement of the holder 200 in the inner tube 150, the legs 220 bend radially inward as a result of contact with the inward-facing surface of the inner tube 150, thus experiencing frictional engagement with the inner tube 150. As force is applied distally along the axis A1 when the receiving head 254 of the bone anchor 250 is loaded onto a distal end of a tool 280, the distally-applied force is received by the legs 220 and distributed outward from the legs 220 to the inner tube 150 to further increase engagement between the two, as illustrated by arrows in FIG. 9. The increased engagement allows for easier loading and extraction of the bone anchor 250 from the holder 200.

Additionally, the legs 220 allow one to visualize and observe an orientation of the threaded shaft 254 during movement of the holder 200 between the legs 220. While two legs 220 are illustrated, more than two legs 220 can be used in other embodiments, such as from two to about twenty. FIGS. 1-4 illustrate surface features 225 that can take a variety of forms and can serve a variety of purposes, such as helping to increase engagement between the holder 200 and the inner tube 150, helping to provide engagement with molds during manufacturing and formation of the holder 200, etc.

Figure 7A:
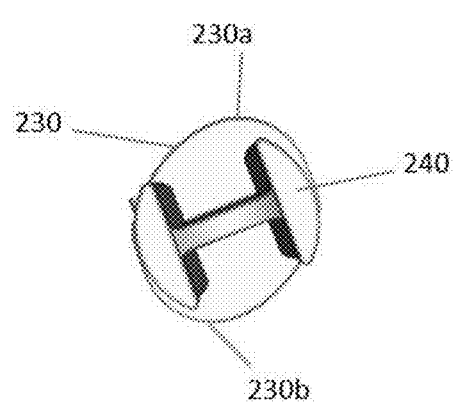
FIG. 7A is a bottom-up view of the implant holder of FIG. 1.
Figure 7B:
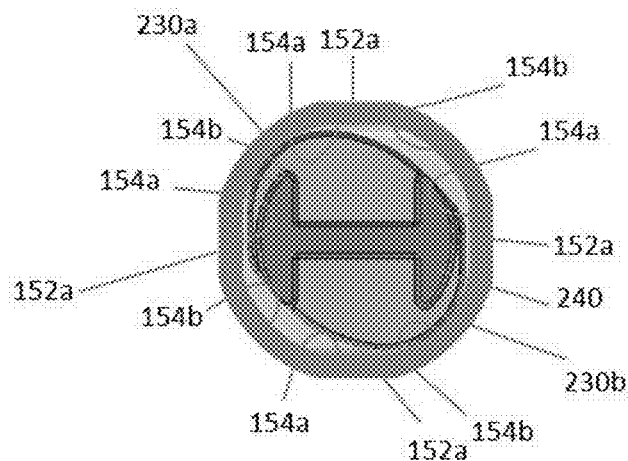
FIG. 7B is a bottom-up view of the implant holder of FIG. 1 inserted into an inner tube.
Figure 8A:
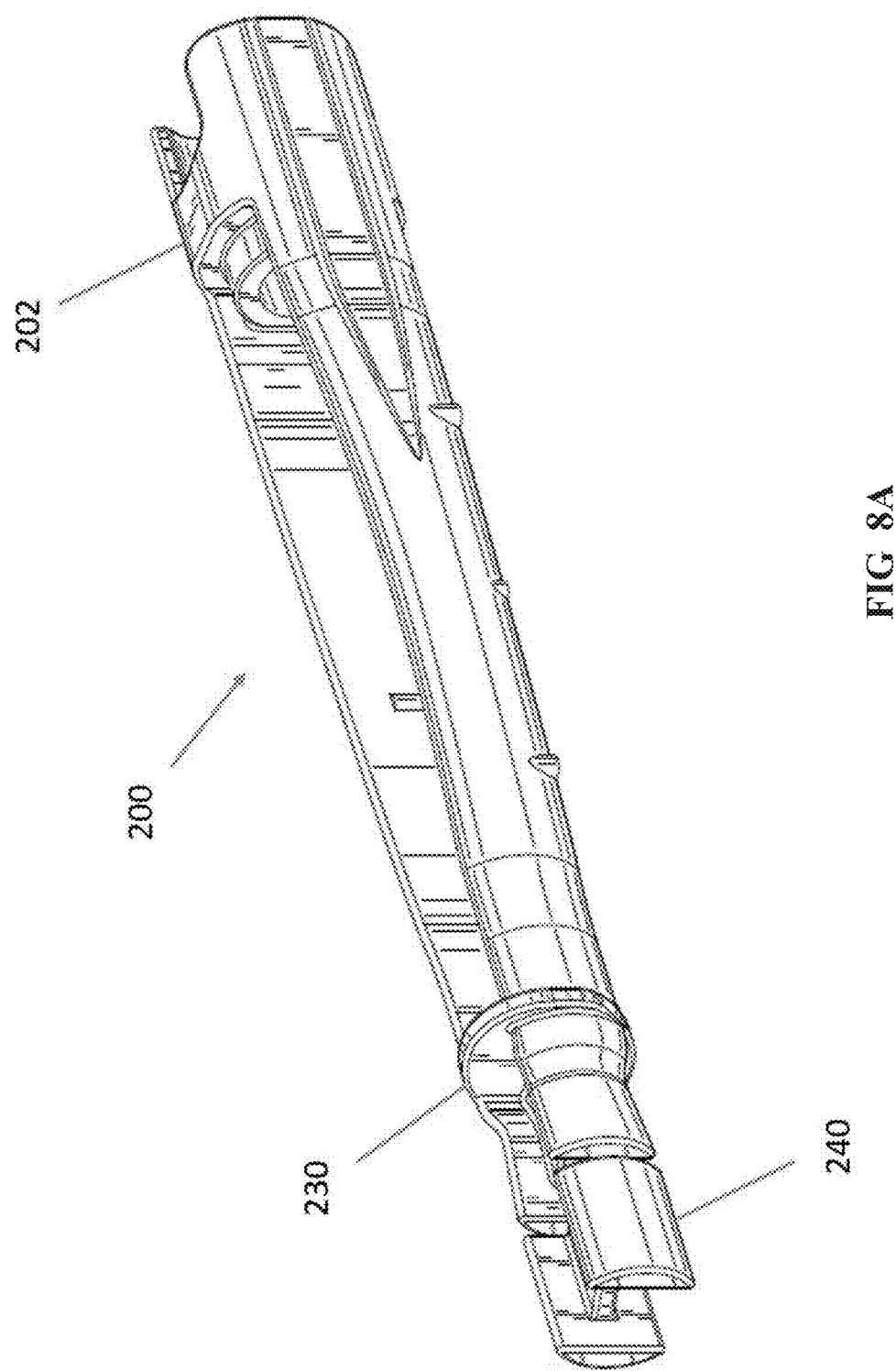
FIG. 8A is a perspective view of the implant holder of FIG. 1.
Figure 8B:
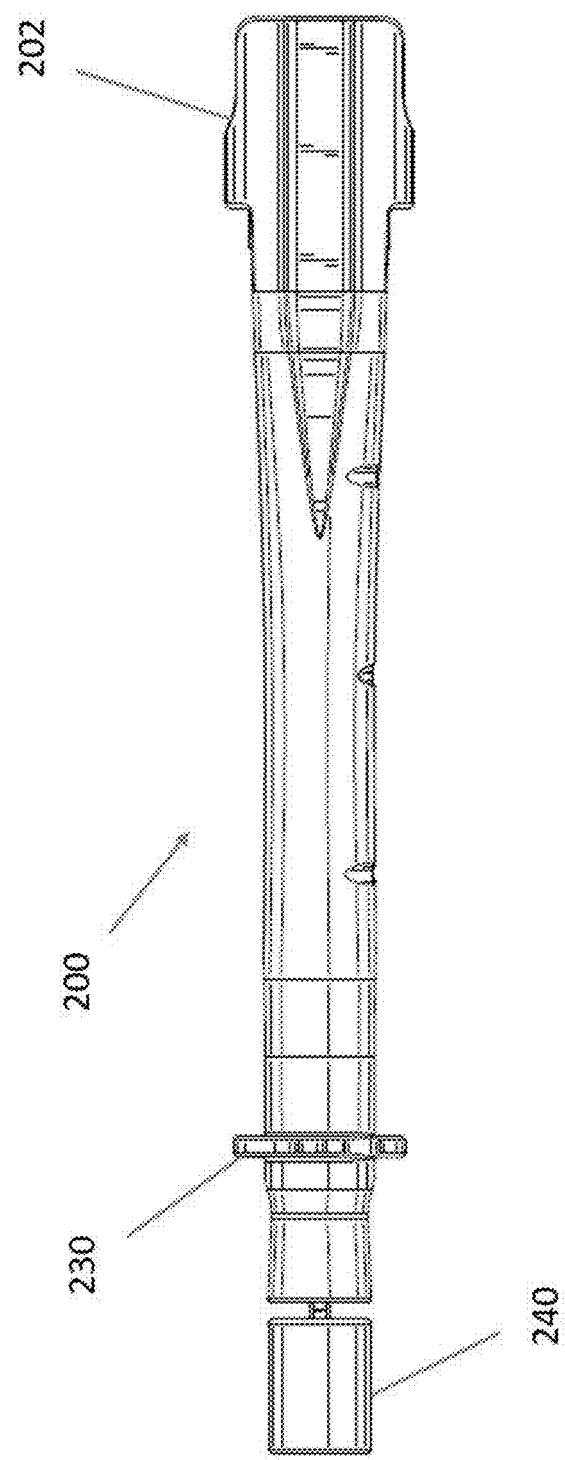
FIG. 8B is a side view of the implant holder of FIG. 1.
Figure 8C:
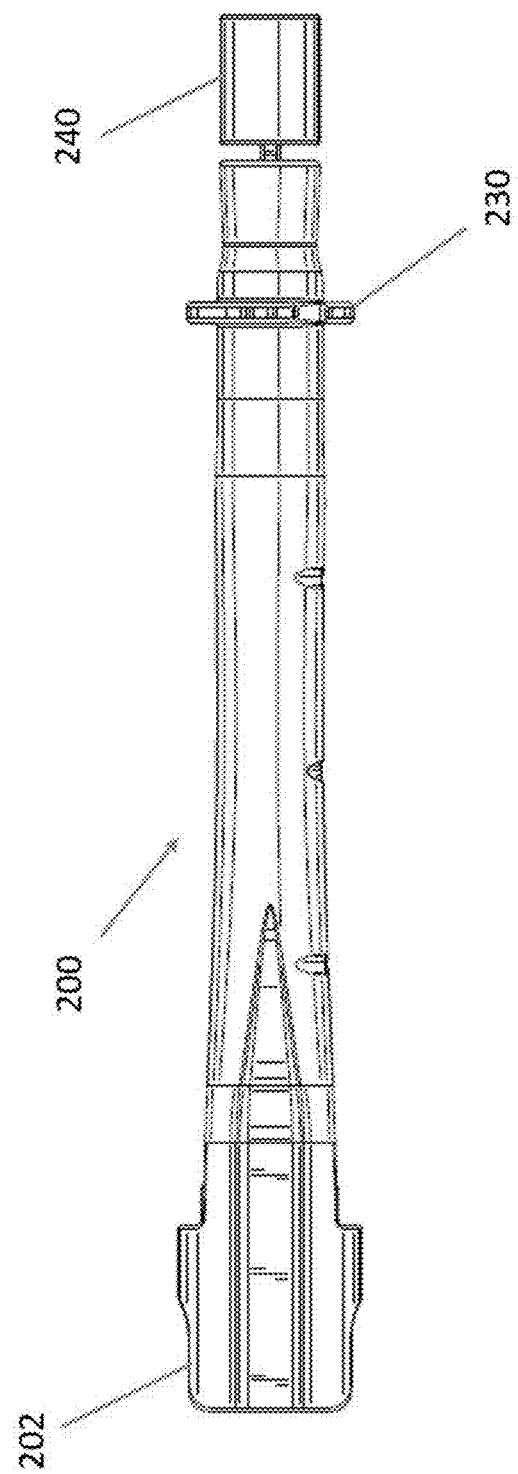
FIG. 8C is another side view of the implant holder of FIG. 1.
Figure 8D:
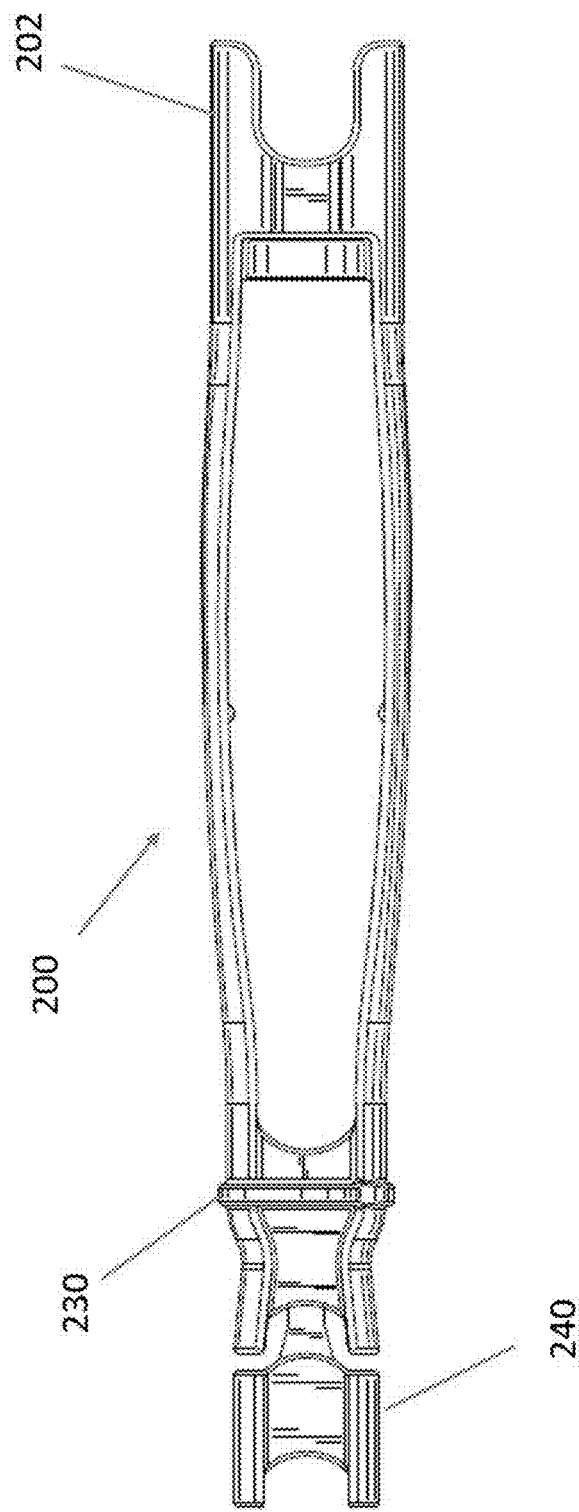
FIG. 8D is a front view of the implant holder of FIG. 1.
Figure 8E:
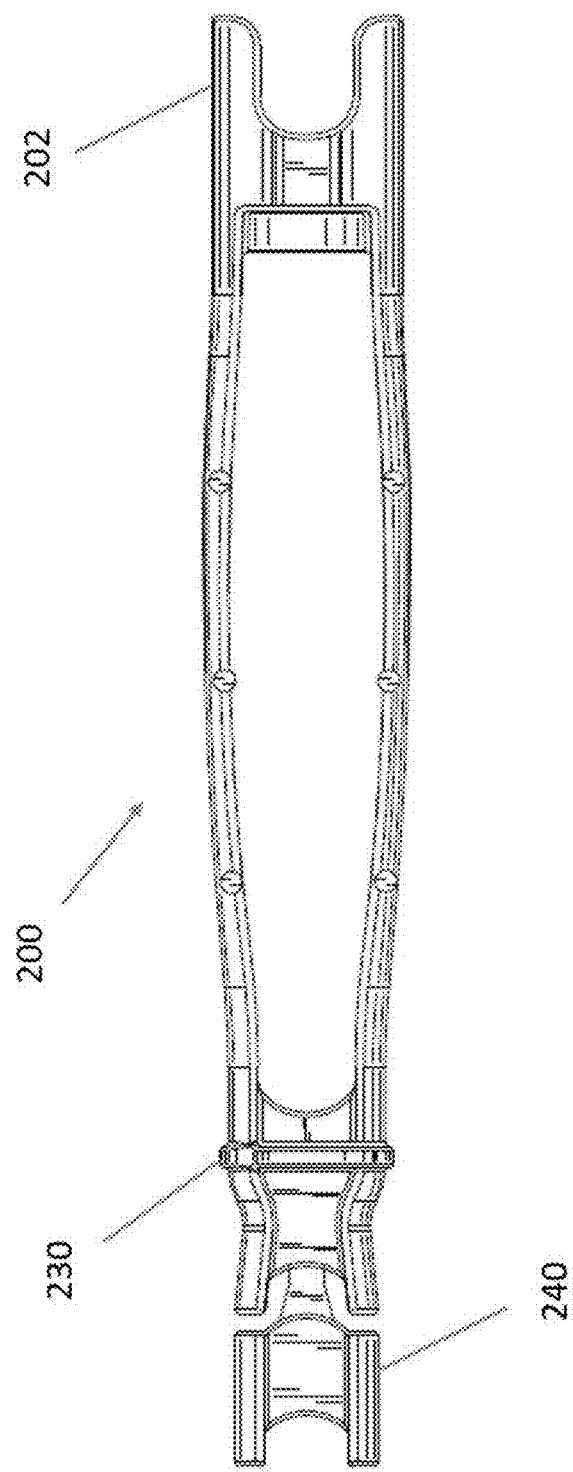
FIG. 8E is a back view of the implant holder of FIG. 1.
Figure 8F:
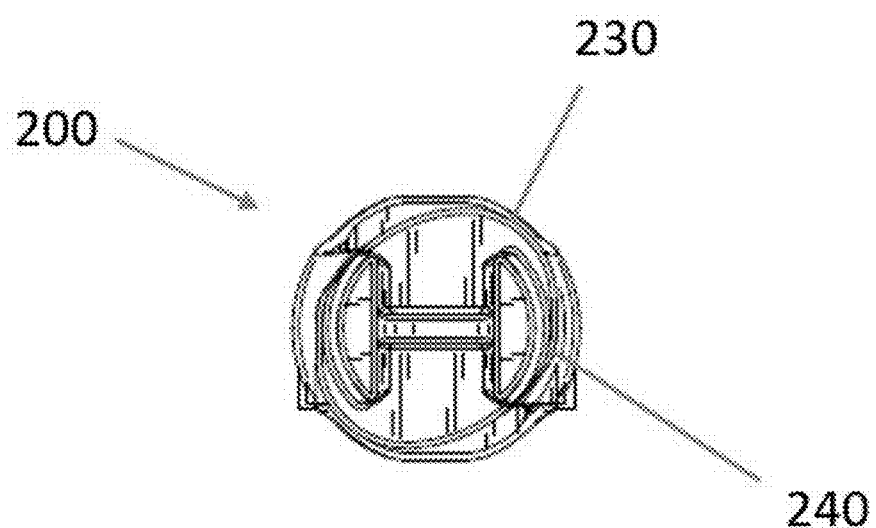
FIG. 8F is a bottom-up view of the implant holder of FIG. 1.
Figure 8G:
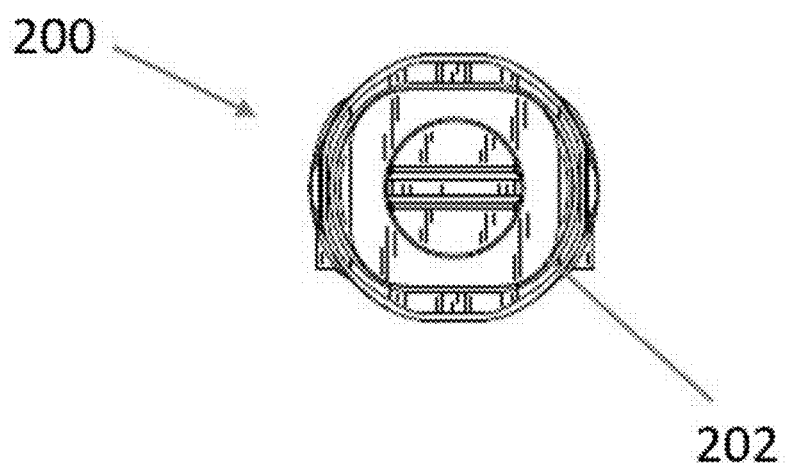
FIG. 8G is a top-down view of the implant holder of FIG. 1.
Figure 8H:
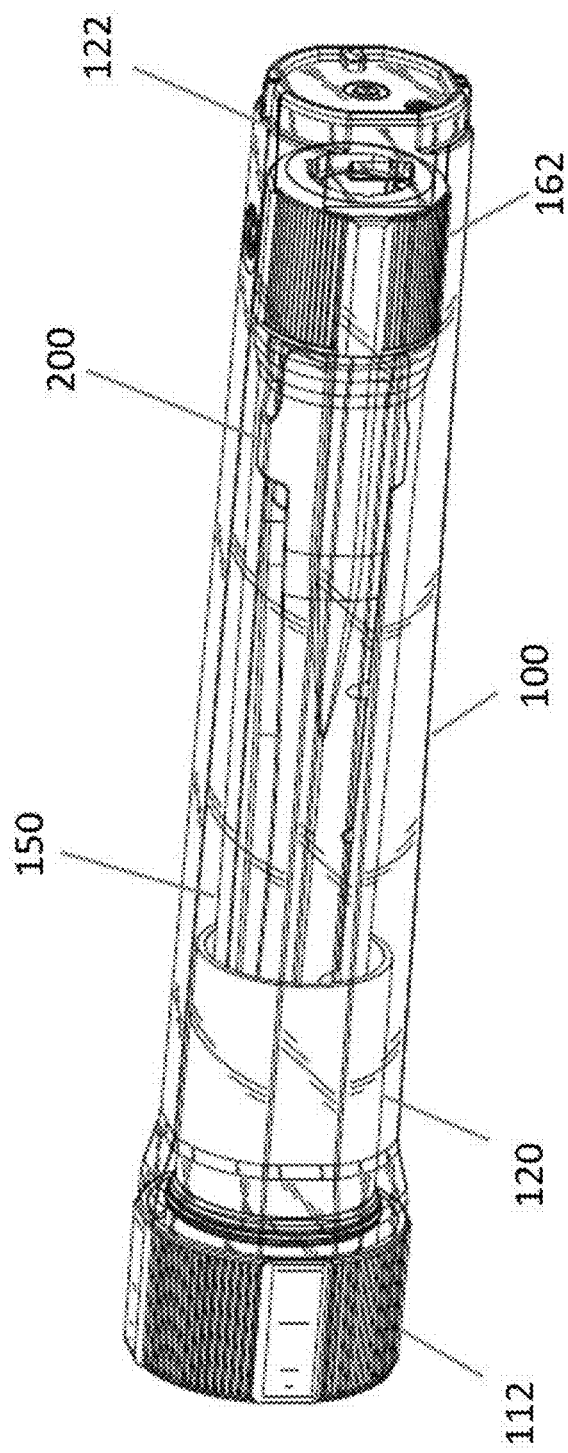
FIG. 8H is a perspective view of the implant holder of FIG. 1 disposed within the inner tube of FIG. 1, which is subsequently disposed within the outer tube of FIG. 1.
Figure 8I:
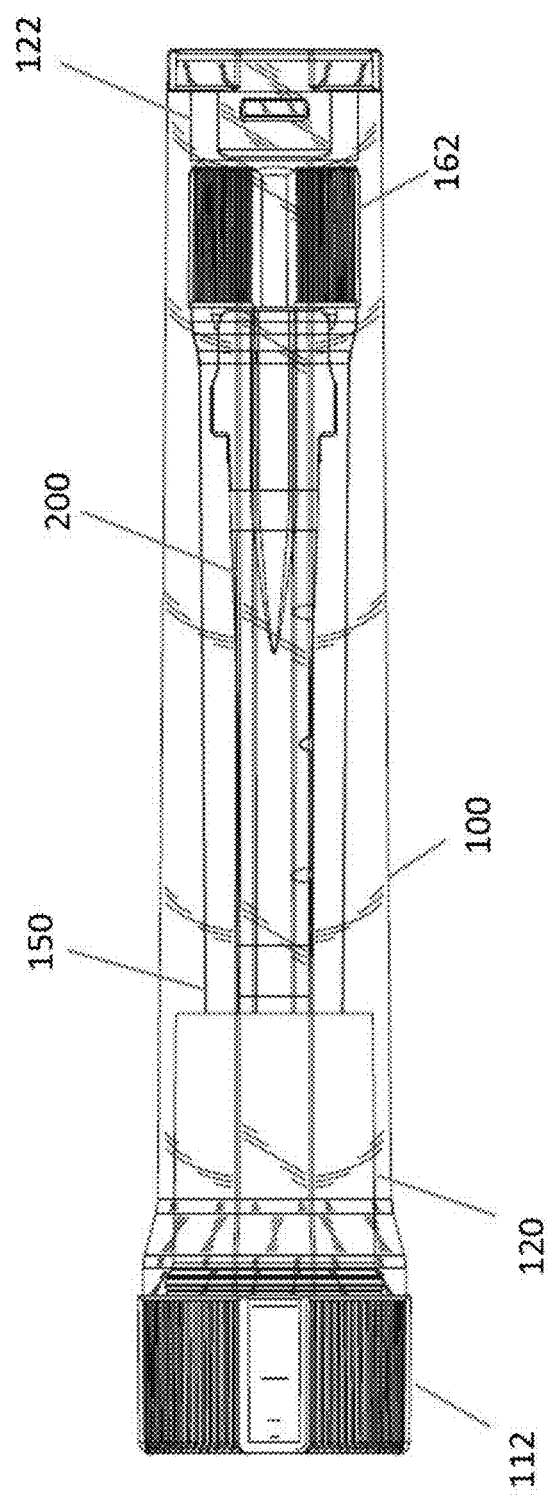
FIG. 8I is a side view of the implant holder, the inner tube, and the outer tube of FIG. 1.
Figure 8J:
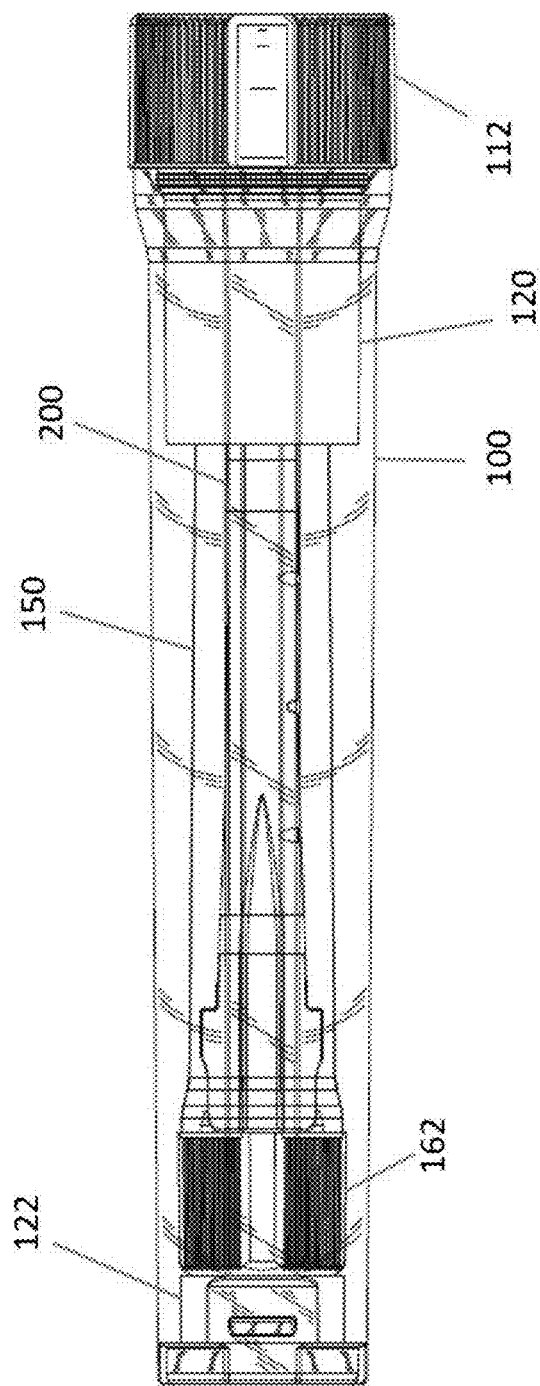
FIG. 8J is another side view of the implant holder, the inner tube, and the outer tube of FIG. 1.
Figure 8K:
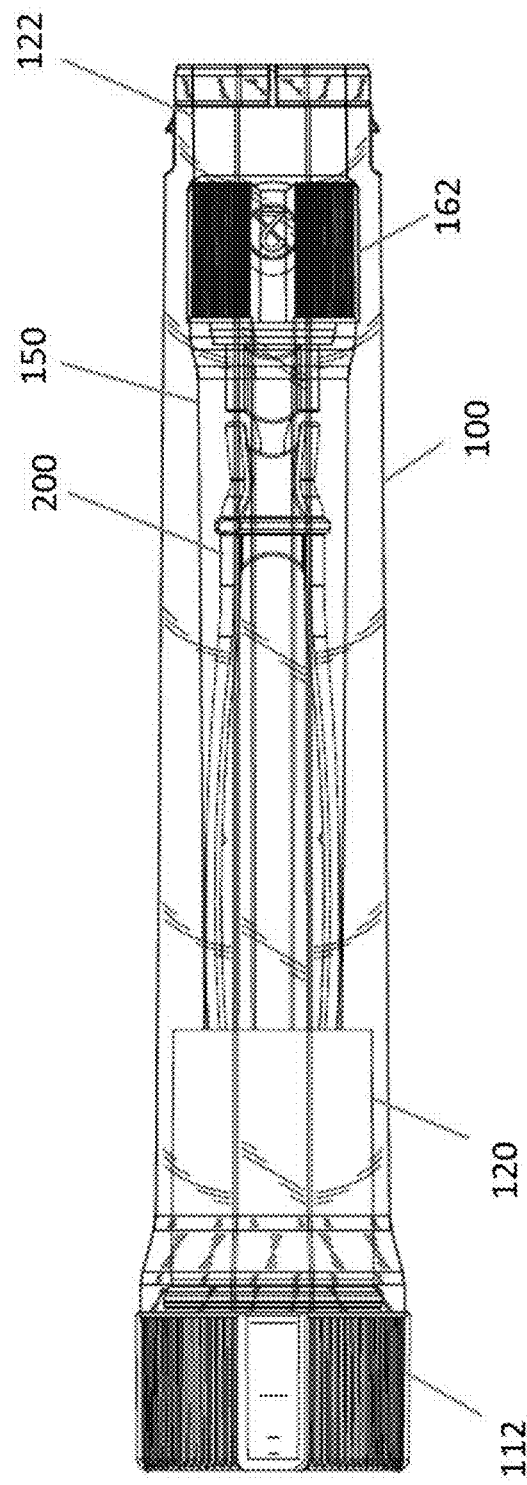
FIG. 8K is a front view of the implant holder, the inner tube, and the outer tube of FIG. 1.
Figure 8L:
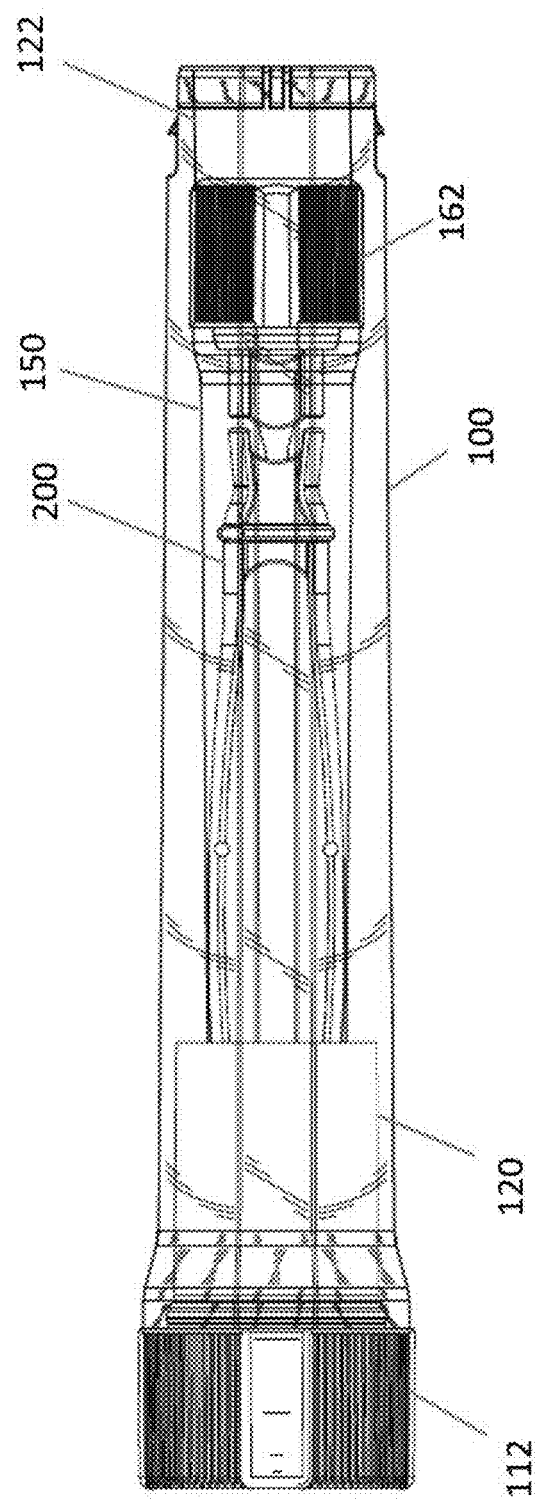
FIG. 8L is a back view of the implant holder, the inner tube, and the outer tube of FIG. 1.
Figure 8M:
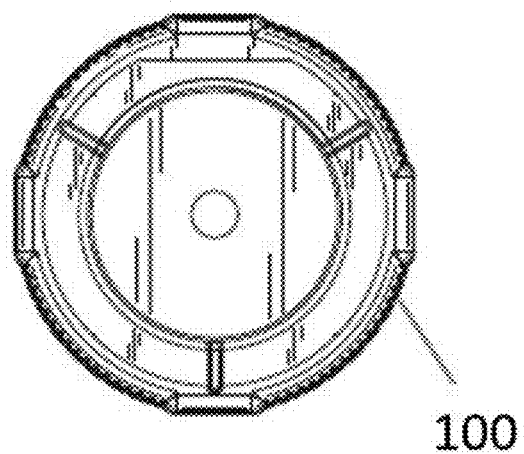
FIG. 8M is a bottom-up view of the implant holder, the inner tube, and the outer tube of FIG. 1.
Figure 8N:
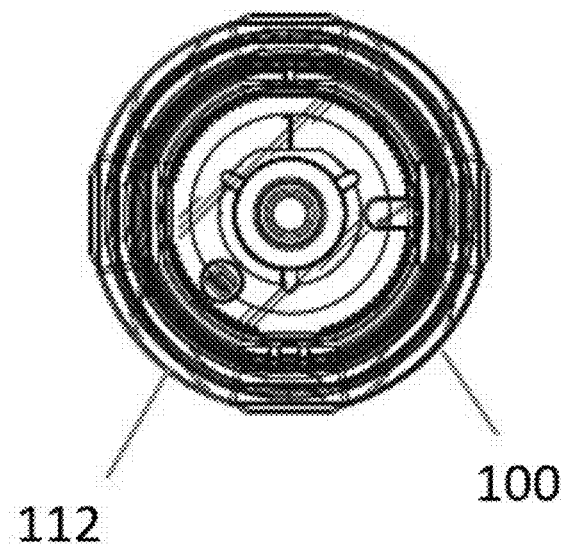
FIG. 8N is a top-down view of the implant holder, the inner tube, and the outer tube of FIG. 1.

The alignment panel 230 is disposed at a distal end of the legs 220 and assists in maintaining an orientation of the holder 200 within the inner tube 150. The alignment panel 230 has a non-circular cross-section taken at a point along the longitudinal axis A1 of the holder 200. As such, at least two sides 230a, 230b of the alignment panel 230 contact inner surfaces 154b of the inner tube 150, as illustrated in FIGS. 7A and 7B. Because the alignment panel 230 is non-circular, the two sides 230a, 230b of the alignment panel 230 that contact the inner tube 150 resist rotation of the holder 200 about the axis A1. While the alignment panel 230 has an oval cross-section, other non-circular shapes can be used, such as squares, triangles, hexagons, octagons, etc.

Figure 10:
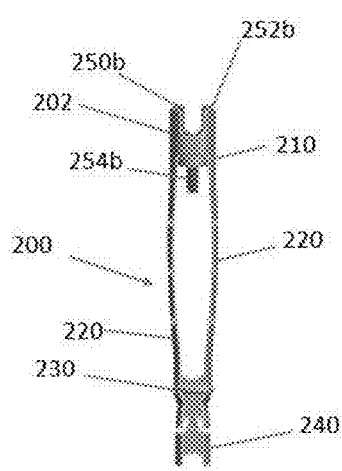
FIG. 10 is a side view of the implant holder of FIG. 1 with another embodiment of a bone anchor.
Figure 11:
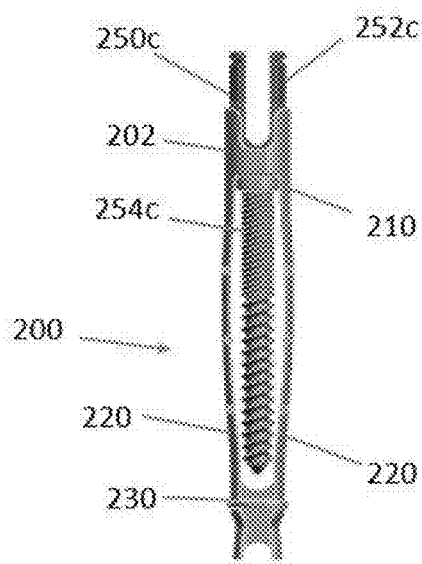
FIG. 11 is a side view of the implant holder of FIG. 1 with another embodiment of a bone anchor.
Figure 12:
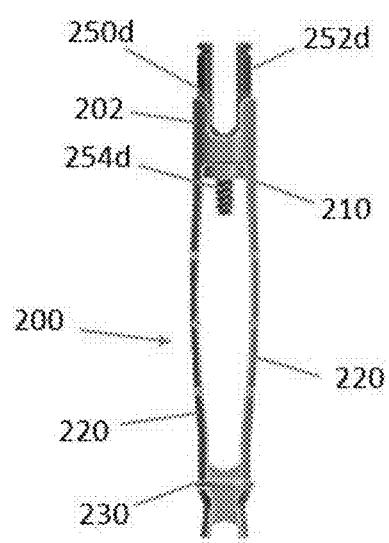
FIG. 12 is a side view of the implant holder of FIG. 1 with another embodiment of a bone anchor.

At a distal-most end of the holder 200, the break-off tab 240 can enable a total length of the holder along the longitudinal axis A1 to be altered. The break-off tab 240 is removable from the holder 200 before placement of the holder 200 into the inner tube 150. Removing the break-off tab 240 creates additional distance between the receiving head 202 and a cap 162 of the inner tube 150. As such, when the break-off tab 240 is removed, bone anchors 250c, 250d with larger driver heads 252c, 252d can be accommodated in the holder 200 while the cap 162 can still close the inner tube 150 and an engagement interface 164 of the cap, discussed additionally below, can still engage the receiving head 200 and the driver heads 252c, 252d to prevent the bone anchor 250 from sliding proximally out of the holder 200, for example if the holder 200 is inverted. As such, with the break-off tab 240 attached, as illustrated in FIGS. 9 and 10, the receiving head 202 of the holder 200 can accommodate a variety of driver heads of various sizes, such as bone anchors 250, 250b with smaller or axially shorter driver heads 252, 252b. Similarly, with the break-off tab 240 removed, as illustrated in FIGS. 11 and 12, the holder 200 can accommodate bone anchors 250c, 250d with larger or axially longer driver heads 252c, 252d.

The illustrated break-off tab 240 is frangibly connected to the holder 200 such that, once the break-off tab 240 is removed, it cannot be reengaged with the holder 200. However, other embodiments can be reengageable, and in some embodiments, various spacers can be added to the inner tube 150 to assist in adjusting placement of the holder 200 within the inner tube 150, either in addition to the break-off tab or instead of it. Additionally, while one break-off tab 240 is illustrated, other embodiments can have a plurality of break-off tabs and/or tabs of different sizes to allow further customization of the axial length of the holder 200.

The holder 200 additionally has one or more feet 245 on distal ends of the holder 200 both with and without the break-off tab 240 attached. The feet 245 assist in maintaining an orientation along the axis A1 of the holder 200 by providing a flat contact surface on which the holder 200 can rest on a distal end of the inner tube 150 when the holder 200 is disposed within the inner tube 150. Furthermore, the holder 200 and its various components can be manufactured in a variety of ways and of a variety of materials. For example, the holder 200 can be manufactured through injection molding, 3D printing, machining, etc., and the holder 200 and/or individual components can be made from various plastics, polymers, metals, etc.

As illustrated in FIGS. 8H-8N and 15-22, the holder 200 can be disposed within the inner tube 150, and the inner tube 150 in turn can be disposed within the outer tube 100. The inner tube 150 assists in maintaining an orientation of the holder 200 within the inner tube 150. As such, the inner tube 150 has an open end 156, a sealed or closed end 158, a lumen 160 extending therebetween into which the holder 200 is inserted, and the cap 162 that closes the open end 156.

The cap 162 is removably engageable with threads 156t on the open end 156, and the cap 162 has the engagement interface 164 on the cap 162 facing the lumen 160 of the inner tube 150. While the illustrated embodiment utilizes threads 156t to engage the cap 162, a variety of engagement mechanisms can be used, such as friction fit, adhesives, etc. The engagement interface 164 removably engages a distal end of the holder 200 and the driver head 252 of the bone anchor 250 when the cap 162 is closed. As discussed above, the engagement interface 164 can thus assist in maintaining the orientation of the bone anchor 150 within the holder 200.

Furthermore, as discussed above, the inner tube 150 has flat inward-facing surfaces 154a that can contact the flat sides 202a, 202b of the receiving head 202 and curved radially inward-facing surfaces 154b that can engage the sides 230a, 230b of the alignment panel 230 to assist in maintaining the orientation of the holder 200 therein. The inner tube 150 and its various components can be manufactured in a variety of ways and of a variety of materials. For example, the inner tube 150 and the cap 162 can be manufactured through injection molding, 3D printing, machining, etc., and the inner tube 150, the cap 162, and/or individual components can be made from various plastics, polymers, metals, etc.

The inner tube 150 can also allow one to visualize and observe an orientation of the bone anchor 250 through the inner tube 150. At least a portion of the inner tube 150 can be made from an optically transparent material. As such, a user can ensure proper orientation of the bone anchor 250 has been maintained during movement, and the user can confirm the contents of the inner tube 150 without being required to open the cap 162, thus maintaining any sterile environment within the inner tube 150.

The inner tube 150 further assists in maintaining the orientation of the inner tube 150 within the outer tube 100. The inner tube 150 has flat outward-facing surfaces 152a that contact corresponding flat inward-facing surfaces on the outer tube 100 to maintain an orientation of the inner tube 150 within the outer tube 100.

As illustrated in FIGS. 18-22, the outer tube 100 can receive the inner tube 150 therein to assist in maintaining an orientation of the inner tube 150. The outer tube 100 has an open end 106, a sealed or closed end 108, a lumen 110 extending therebetween into which the inner tube 150 can be inserted, and a cap 112 that closes the open end 106.

The cap 112 is removably engageable with threads 106t on the open end 106, and the cap 112 has an engagement interface 120 that protrudes from a surface of the cap 112 into the lumen 110 of the outer tube 100 when the cap 112 closes the open end 106. While the illustrated embodiment utilizes threads 106t to engage the cap 112, a variety of engagement mechanisms can be used, such as friction fit, adhesives, etc. The engagement interface 120 removably engages the closed end 158 of the inner tube 150 prior to the cap 112 closing the open end 106. As such, the inner tube 100 is held by and protrudes from the cap 112. An additional spacer 122 is also inserted into the lumen 110 against an inner surface of the closed end 108. The additional spacer 112 assists in engaging the cap 162 of the inner tube 15. As such, the inner tube 150 is held between the spacer 122 on one end and the engagement interface 120 on the other. Both the engagement interface 120 and the spacer 122 can engage the inner tube 150 through a friction or press fit.

As discussed above, the outer tube 100 has flat inward-facing surfaces 102 that can contact the corresponding flat outward-facing surfaces 152a of the inner tube 150 to maintain an orientation of the inner tube 150. However, in some embodiments, the engagement mechanism 120 and/or the spacer 122 can contact the inner tube 150 while the inward-facing surfaces 102 of the outer tube 100 do not contact the inner tube 150. The outer tube 100 and its various components can be manufactured in a variety of ways and from a variety of materials. For example, the outer tube 100 and the cap 112 can be manufactured through injection molding, 3D printing, machining, etc., and the outer tube 100, the cap 112, and/or individual components can be made from various plastics, polymers, metals, etc.

Similar to the inner tube 150, the outer tube 100 can also allow one to visualize and observe an orientation of the bone anchor 250 therethrough. Thus, at least a portion of the outer tube 100 can be made from an optically transparent material. As such, a user can ensure proper orientation of the bone anchor 250 has been maintained during movement, and the user can confirm the contents of the outer tube 100 without being required to open the cap 112, thus maintaining any sterile environment therewithin.

Figure 13:
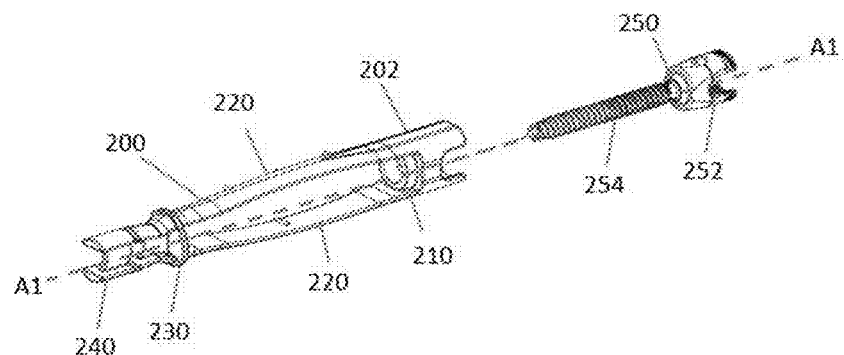
FIG. 13 is a perspective view of the implant holder and bone anchor of FIG. 1.
Figure 14:
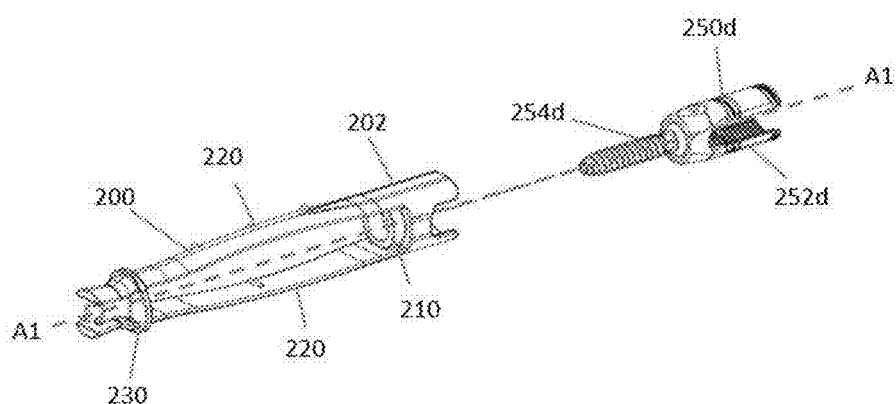
FIG. 14 is a perspective view of the implant holder and bone anchor of FIG. 11.

In use, a user can insert the bone anchor 250 into the holder 200. As illustrated in FIGS. 13 and 14, bone anchors with various driver heads and various threaded shafts can be used, and a user can remove the break-off tab 240 as needed to ensure each driver head fits securely within a space between the receiving head 202 of the holder 200 and the cap 162 of the inner tube 150. Because the space between the receiving head 202 and the cap 162 can be customized to a particular driver head through use of the break-off tab 240, each bone anchor can remain in the holder 200 during movement of the inner and outer tubes 100, 150, even upon inversion of the entire implant holding system.

Figure 15:
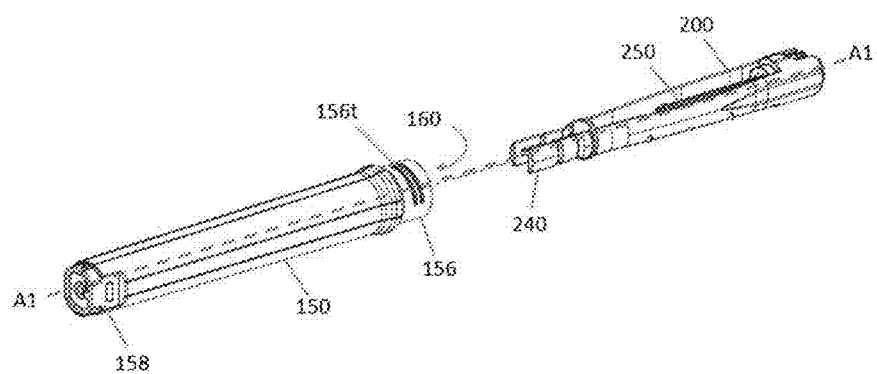
FIG. 15 is a perspective view of the implant holder and bone anchor of FIG. 13 being inserted into an inner tube.
Figure 16:
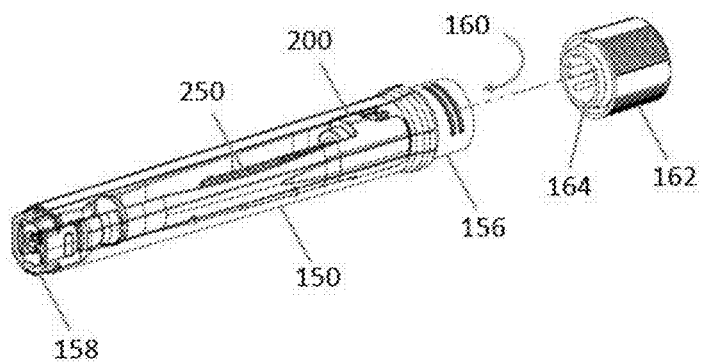
FIG. 16 is a perspective view of the implant holder, bone anchor, and inner tube of FIG. 15.
Figure 17:
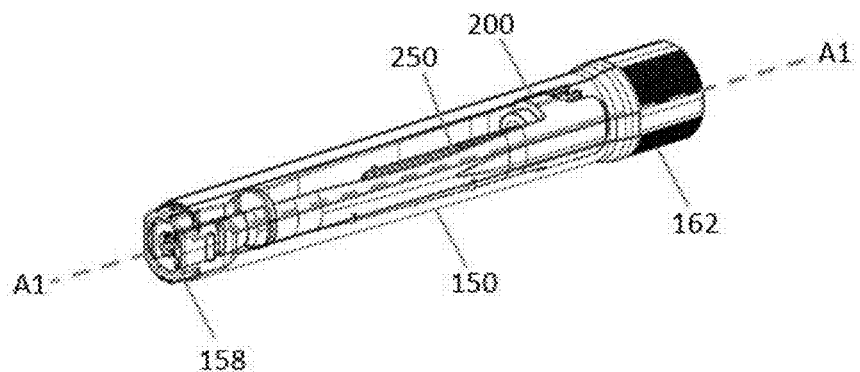
FIG. 17 is a perspective view of the implant holder, bone anchor, and inner tube of FIG. 15.
Figure 18:
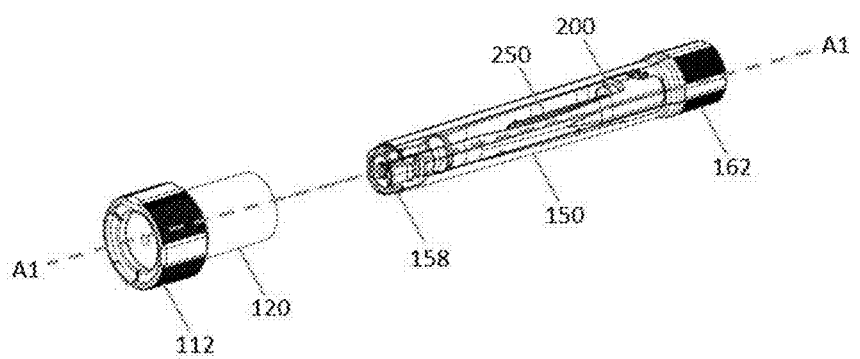
FIG. 18 is a perspective view of the implant holder, bone anchor, and inner tube of FIG. 15 with a cap of an outer tube.
Figure 19:
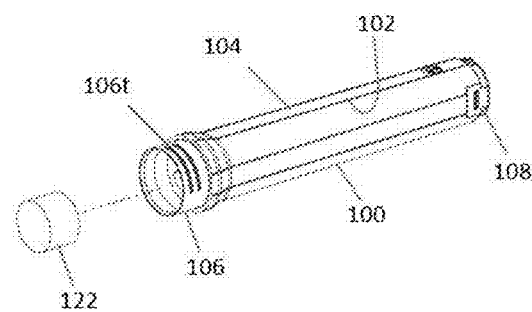
FIG. 19 is a perspective view of one embodiment of an outer tube.
Figure 20:
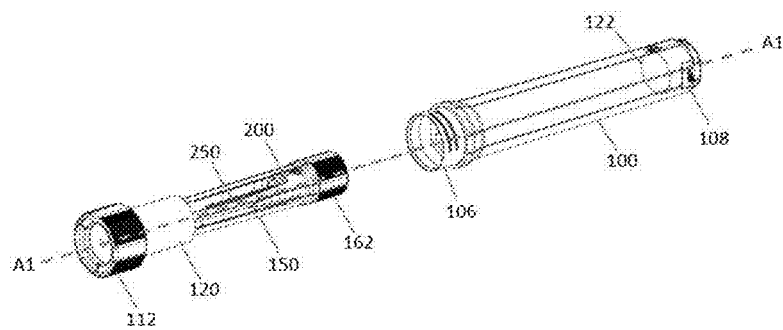
FIG. 20 is a perspective view of the implant holder, bone anchor, inner tube, and cap of FIG. 18 with the outer tube of FIG. 19.
Figure 21:
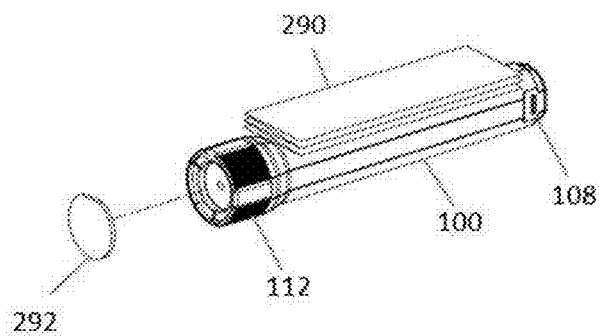
FIG. 21 is a perspective view of the outer tube of FIG. 19.
Figure 22:
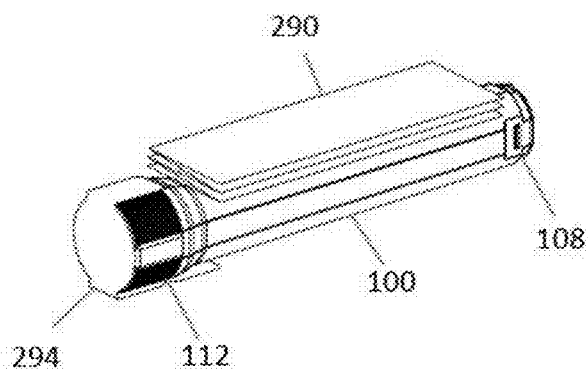
FIG. 22 is a perspective view of the outer tube of FIG. 19.

As illustrated in FIGS. 15-17, the holder 200 is inserted into the open end 156 of the inner tube 150 and into the lumen 160, and the legs 220 of the holder 200 engage the radially inward-facing surfaces of the inner tube 150 to maintain the orientation of the holder 200 when the holder 200 has been fully inserted. The cap 162 is placed on the open end 156 of the inner tube 150 to enclose the holder 200 and the bone anchor 250. As illustrated in FIGS. 18-22, the closed end 158 of the inner tube 150 is placed in engagement with the engagement mechanism 120 of the cap 112, and the spacer 122 can be inserted into the lumen 110 of the outer tube 100. The inner tube 150 and the engagement mechanism 120 are inserted into the open end 106 of the outer tube 100, and the cap 112 is placed on the open end 106 of the outer tube 100 to enclose the inner tube 150. The outer tube 100, the inner tube 150, and the holder 200 can all thus be coaxial once the implant holding system is assembled. Various labels, seals, tamper-proof closures, etc. 290, 292, 294 can be applied to the outer tube 100, and the implant holding system is thus prepared for transportation and eventual deployment of the bone anchor 250.

Figure 23:
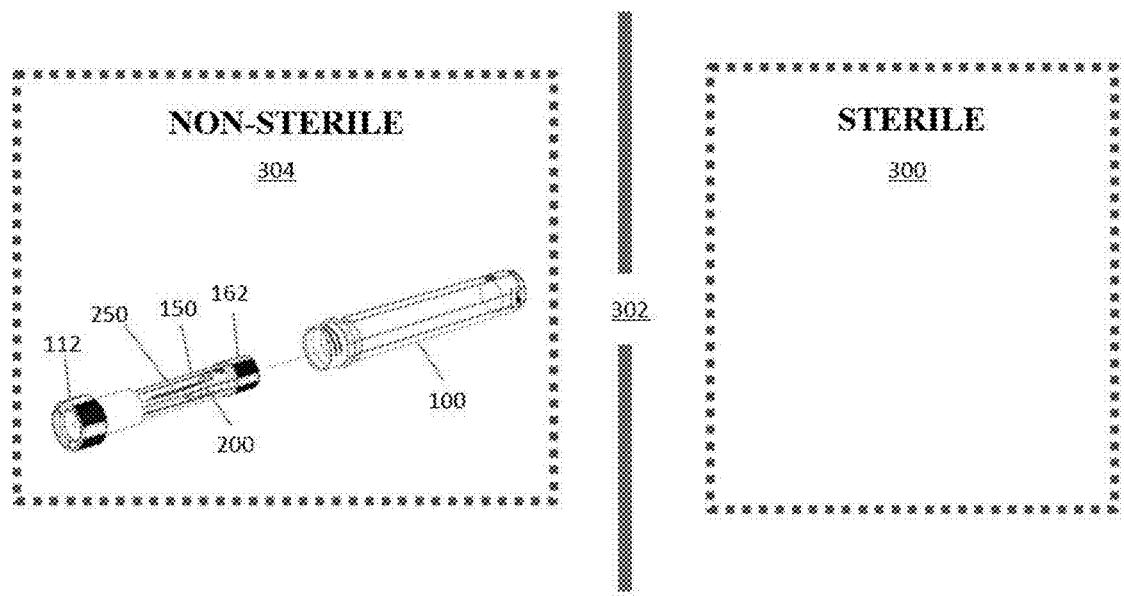
FIG. 23 is a diagram of one embodiment of steps for passing the inner tube of FIG. 20 into a sterile environment.
Figure 24:
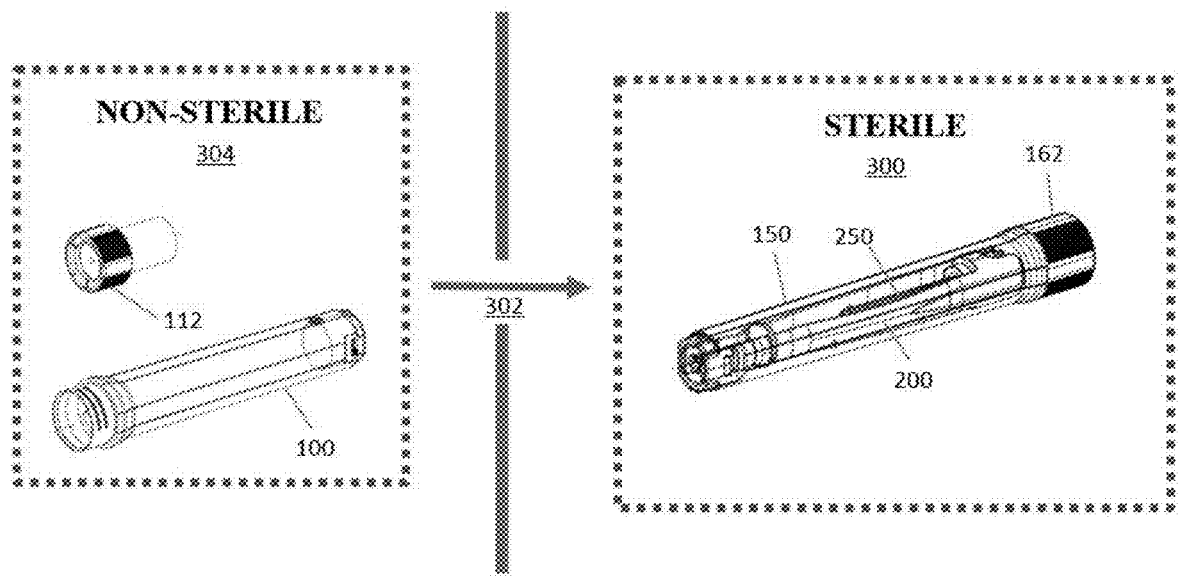
FIG. 24 is another diagram of the steps of FIG. 20 for passing the inner tube into a sterile environment.

Furthermore, one or more components of the system can be sterilized at various points throughout the assembly process. For example, the outer tube 100, inner tube 150, holder 200, and bone anchor 250 can be sterilized and assembled in a sterile environment. As such, the holder 200 and the bone anchor 250 can be placed in a sterile enclosure within the inner tube 150, and the inner tube 150 can then be placed within a sterile enclosure within the outer tube 100. As the outer tube 100 is transported to a deployment site, such as an operating room, outer surfaces 104 of the outer tube can be contaminated and no longer sterile. However, an interior environment of the outer tube 100 and the inner tube 150, the holder 200, and the bone anchor 250 are all still sterile. Thus during deployment, a sterile operating environment 300 can be prepared, and an opening or passageway 302 between an external, non-sterile environment 304 and the sterile environment 300 can be formed, as illustrated in FIGS. 23 and 24. A user in the non-sterile environment 304 can open the outer tube 100 and pass or drop the inner tube 150 through the passageway 302 into the sterile environment 300. A user in the sterile environment 300 can then open the inner tube 150 within the sterile environment 300 and extract the bone anchor 250 without having to sterilize the bone anchor 250 because the sterility of the inner tube 150, the holder 200, and the bone anchor 250 have all been maintained. The user can thus use an exact number and type of bone anchors actually needed during an operation without having to sterilize a large number of additional bone anchors and/or without having to store, maintain, and utilize any excess sterilization equipment.

Additionally, because the holder 200 has maintained an orientation of the bone anchor 250 during transportation, when the cap 162 is removed from the inner tube 150, the bone anchor 250 can be removed from the inner tube 150 and the holder 200 by inverting the inner tube 150 or through use of various tools without encountering an axially misaligned bone anchor 250 that may be difficult to remove. Various tools can be used, such as the tools discussed in US Patent App. No. 2019/0150989 of Biester et al., further identified and incorporated by reference above.

While the holder 200 provided above can maintain orientations of driver heads and threaded shafts of various bone anchors together, other embodiments of holders can secure either the threaded shaft or various modular elements of the driver head separately. For example, FIGS. 25-40 illustrate numerous embodiments of holders that secure threaded shafts of various bone anchors that have different lengths, diameters, and configurations.

Figure 25:
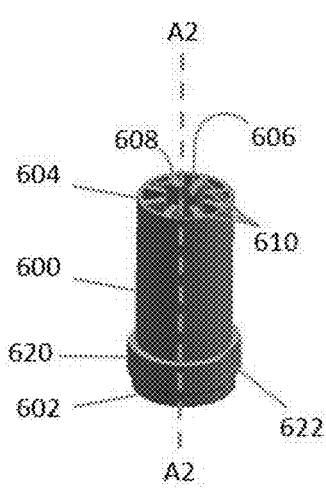
FIG. 25 is a perspective view of another embodiment of an implant holder.
Figure 26:
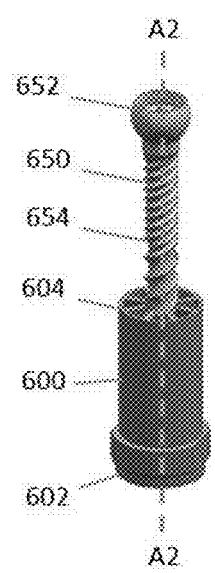
FIG. 26 is a perspective view of the implant holder of FIG. 25 with another embodiment of a bone anchor.
Figure 27:
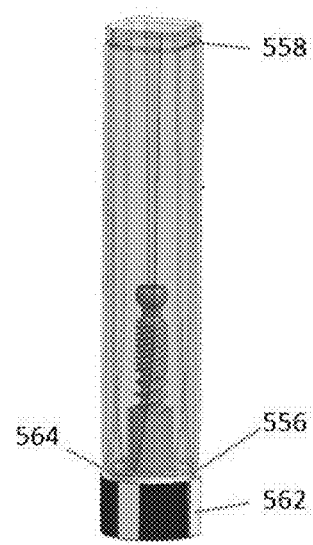
FIG. 27 is a perspective view of the implant holder of FIG. 25 inserted into an inner tube.

FIGS. 25-27 illustrate a holder 600 similar to holder 200 that maintains an orientation of a threaded shaft 654 of a bone anchor 650 relative to the holder 600. The holder 600 is placed within an inner tube 550 similar to inner tube 150 and within an outer tube similar to outer tube 100.

The bone anchor 650 has a driver head 652 that can receive additional modular head components thereon in use, similar to the bone anchors discussed above and incorporated herein. However, various other bone anchors can be used, as well, such as fixed screws.

The holder 600 has a closed first end 602 with an engagement base 620, an open second end 604, and a lumen extending at least partially therebetween. The lumen 606 receives at least part of the threaded shaft 654 of the bone anchor 650. A plurality of alignment members 610 extend into the lumen 606 to engage the threaded shaft 654 of the bone anchor 650 to maintain an orientation of the threaded shaft 654 relative to a central longitudinal axis A2 of the holder 600. The alignment members 610 are rectangular structures that protrude from an inward-facing surface 608 of the lumen 606 towards the axis A2. The members 610 also extend along an entire length of the lumen 606 parallel to the axis A2. As the threaded shaft 654 is inserted into the lumen 606, ends of the alignment members 610 closest to the central axis A2 contact the threaded shaft 654 and are forced to bend and flex away from the threaded shaft 654. As such, the threaded shaft 654 is held in the lumen 606 by the alignment members 610 through a friction fit such that an orientation of the threaded shaft 654 is maintained relative to the holder 600. The alignment members 610 and the holder 600 as a whole can be made from a variety of materials, such as various plastics, polymers, etc. Additionally, while the alignment members 610 are shown to be distributed evenly around the lumen 606, different distribution patterns and arrangements are possible. The lumen 606 of the holder 600 also has a circular cross-section, but a variety of cross-sections are possible, such as triangular, rectangular, etc.

The lumen 606 terminates in the closed first end 602 with the engagement base 620. The engagement base 620 securely engages the holder 600 with an engagement mechanism 564 of a cap 562 of inner tube 550, similar to engagement mechanism 164 of cap 162. When the cap 562 closes the inner tube 550, discussed below, the holder 600 protrudes from the cap 562 and into a lumen 560 of the inner tube 550. The engagement base 620 continues to maintain its engagement with the engagement mechanism 564 when the cap 562 is removed from the inner tube 550. As such, the holder 600 maintains its orientation relative to the cap 562, including rotating about the axis A2 when the cap 564 is removed from the inner tube 550.

The engagement base 620 is inserted into a cavity of the engagement mechanism 564 on the cap 562 in a secure friction fit, and the base 620 has one or more flat outward-facing surfaces 622 that correspond to flat inward-facing surfaces on the engagement mechanism 564. As such, rotation of the holder 600 is prevented about the axis A2 relative to the cap 562. In other embodiments, various different engagement methods are possible, however, such as through clips, hooks, adhesives, tabs, etc., and engagement can be permanent or removable.

The holder 600 can thus be inserted into the inner tube 550 when the holder 600 protrudes from the cap 562 of the inner tube 550. The inner tube 550 has a lumen extending between a first open end 556 into which the holder 600 is inserted and a second sealed or closed end 558. As discussed above, the cap 562 is engageable with the inner tube 550 to close the open end 556 of the inner tube 550. The cap 562 engages threads on the open end 556 similar to the threads 156t of the inner tube 150 discussed above. However, a variety of different closure mechanisms can be used, such as friction fit, hooks, adhesive, etc.

Except through contact with the cap 562, the inner tube 550 thus does not contact the holder 600. However, the inner tube 550 has flat outward-facing surfaces that can engage with radially inward-facing surfaces of an outer tube, such as tube 100. The inner tube 550 additionally can also be secured between the engagement mechanism 120 and the spacer 122. Similar to inner tube 150, in some embodiments, radially inward-facing and outward-facing surfaces of the outer and inner tubes 100, 550 do not contact one another, and the inner tube 550 in some embodiments can be secured within the outer tube 100 by the engagement mechanism 120 and the spacer 122.

Additionally, the holder 600 and the inner tube 550 can allow one to visualize the bone anchor 650 because the holder 600 receives a portion of the bone anchor 650 that is less than the entire bone anchor 650 and at least part of the inner tube 550 can be made of an optically clear material. Additionally, the holder 600 and the inner tube 550 can be sterilized, loaded, transported, and opened for deployment of the bone anchor 650 similar to the holder 200 and the inner tube 150.

As referenced above, a variety of different alignment members can be used, as illustrated throughout FIGS. 28-40, that can have different structures and engagement methods and that can be made from rigid or flexible materials depending on the embodiment, such as metals, plastics, polymers, etc.

For example, FIGS. 28-31 illustrate embodiments of alignment members 702, 706, 710, 714 of holders 700, 704, 708, 712 that have similar rectangular structures to the alignment members 610. However, the alignment members 702, 706, 710, 714 protrude to different lengths towards a longitudinal axis of each holder 700, 704, 708, 712, with some alignment members providing greater amounts of unobstructed space within the holders for receiving threaded shafts of bone anchors, such as threaded shaft 718 of bone anchor 716, that have increased diameters and thus may require additional unobstructed space. FIGS. 32-34 illustrate another embodiment of a holder 720 with alignment members 722 that extend proximal to a central longitudinal axis A3 of the holder 720 and are in the form of rigid trapezoidal structures aligned to form broken ribbing to engage threading on threaded shafts. As such, a threaded shaft 734 on a bone anchor 730 can be inserted into the lumen of the holder 720 and into secure engagement with the alignment members 722. As illustrated in FIGS. 33 and 34, a cannula 728 is formed at least partially through an engagement base 726 that is similar to engagement base 620 above and can be engaged with a cap 730. However, the cannula 728 can receive a stylet 734 through a threaded cannulated shank 752 of a bone anchor 750 for use with an inserter 740, for example the Viper Prime Inserter. In other embodiments, a cannula may be formed to receive a distal-most end of a bone anchor.

Figure 35:
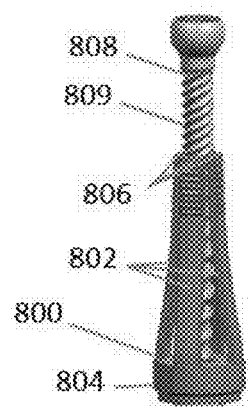
FIG. 35 is a perspective view of another embodiment of an implant holder.
Figure 36:
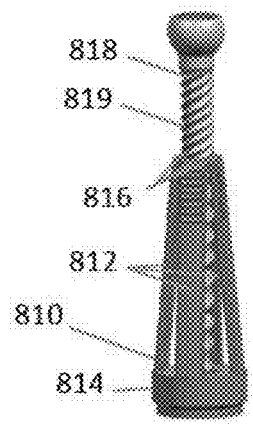
FIG. 36 is a perspective view of another embodiment of an implant holder.
Figure 37:
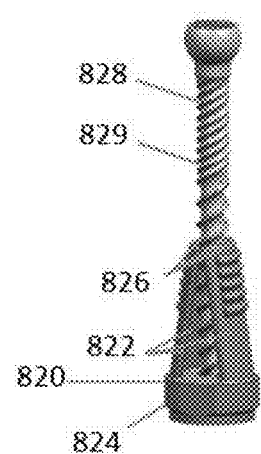
FIG. 37 is a perspective view of another embodiment of an implant holder.

FIGS. 35-37 illustrate additional embodiments of holders 800, 810, 820 with alignment members 802, 812, 822. The alignment members 802, 812, 822 are generally rectangular structures that extend or protrude at a radially inward angle or slope from respective engagement bases 804, 814, 824 towards a central longitudinal axis of each holder 800, 810, 820 and into a lumen of an inner tube when the holders 800, 810, 820 are engaged with caps and inserted into an inner tube, such as the inner tube 550. The alignment members 802, 812, 822 are joined only on one rectangular edge to the engagement bases 804, 814, 824 and are unattached on the other three rectangular edges. However, because the members 802, 812, 822 extend radially inward at an angle, they form engagement edges 806, 816, 826 that engage threaded shafts 809, 819, 829 of bone anchors 808, 818, 828 to secure the bone anchors 808, 818, 828 therein and maintain orientations of the bone anchors 808, 818, 828 in the holders 800, 810, 820.

Figure 38:
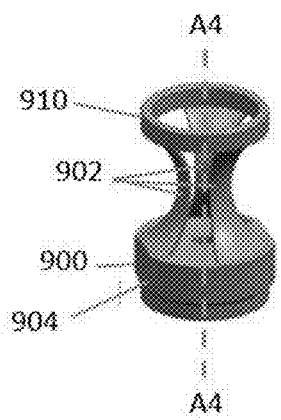
FIG. 38 is a perspective view of another embodiment of an implant holder.
Figure 39:
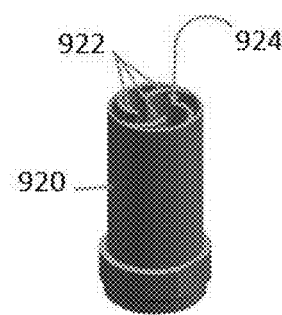
FIG. 39 is a perspective view of another embodiment of an implant holder.

FIG. 38 illustrates another embodiment of a holder 900 with alignment members 902. The alignment members 902 are bowed or curved arms that curve toward a central longitudinal axis A4 and extend between an engagement base 904 with a partial cannula 906 and an upper ring 910 through which a threaded shaft of a bone anchor is inserted. FIG. 39 illustrates still another embodiment of alignment members 922 of a holder 920 that extend along an inner surface of a lumen 924 of the holder 920, similar to the alignment members 610. However, the alignment members 922 protrude into the lumen 924 in a helical or spiral pattern.

Figure 40:
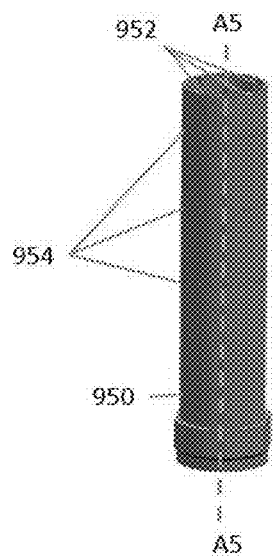
FIG. 40 is a perspective view of another embodiment of an implant holder.

Additionally, holders configured to secure threaded shafts of bone anchors can have variable longitudinal lengths, similar in configuration to the break-off tab 240 of the holder 200. As illustrated in FIG. 40, a holder 950 with alignment members 952 and a longitudinal axis A5 can have one or more perforated rings 954 extending around the holder 950 at various points along the axis A5 such that the holder 950 is a series of portions that are frangibly engaged with each other. A length of the holder 950 along the axis A5 can be shortened to better fit a length of a threaded shaft of a bone anchor by removing one or more portions at a selectable ring 954.

Figure 41:
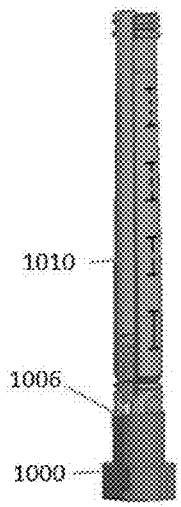
FIG. 41 is a perspective view of another embodiment of an implant holder.
Figure 42:
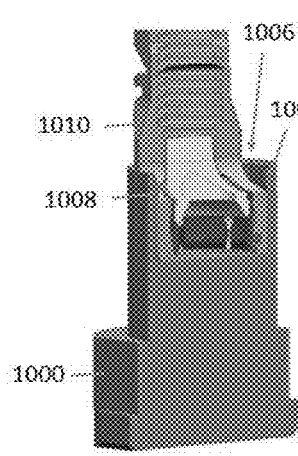
FIG. 42 is a cross-sectional side view of the holder of FIG. 41.
Figure 43:
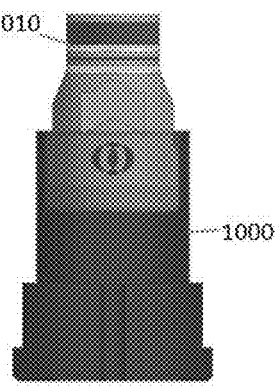
FIG. 43 is a partially transparent side view of the holder of FIG. 41.
Figure 55:
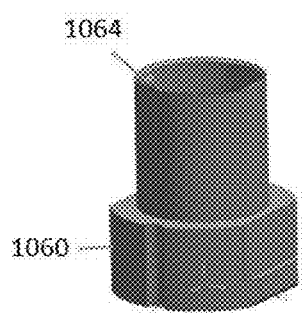
FIG. 55 is a perspective view of another embodiment of an implant holder.
Figure 56:
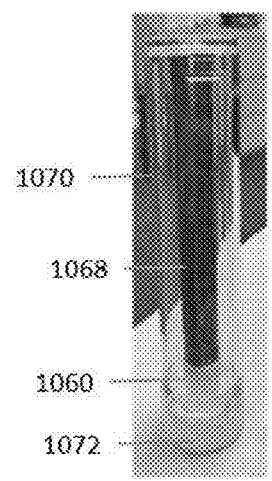
FIG. 56 is a perspective view of the holder in FIG. 55 inserted into an inner tube.
Figure 57:
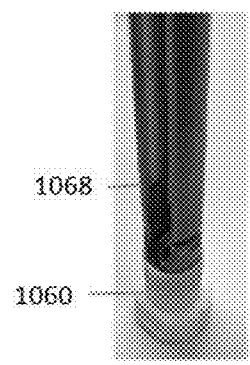
FIG. 57 is a perspective view of the holder in FIG. 55 inserted into a cap.
Figure 58:
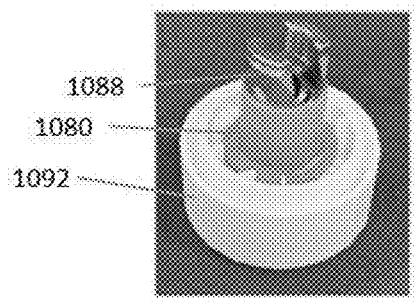
FIG. 58 is a perspective view of an embodiment of an implant holder engaged with a cap.
Figure 59:
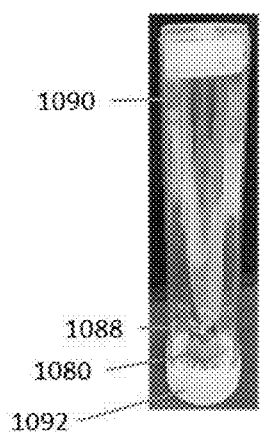
FIG. 59 is a perspective view of the holder in FIG. 58 inserted into an inner tube.
Figure 60:
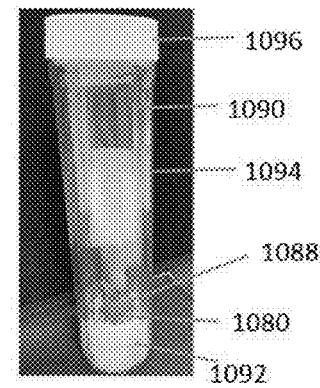
FIG. 60 is a perspective view of the holder and the inner tube in FIG. 59 inserted into an outer tube.

Holders can also secure orientations of modular components of various bone anchors with driver heads similar to securing threaded shafts, as illustrated in FIGS. 41-60. For example, FIGS. 41-43 illustrate one embodiment of a holder 1000 that receives a receiver member or driver head 1010 designed to be used with various threaded shafts in one or more modular screw arrangements, such as those provided in US Patent App. No. 2019/0150989 of Biester et al., further identified and incorporated by reference above. The holder 1000 is similar to holder 600 and can receive the head 1010 in a lumen 1006 of the holder 1000. As illustrated in FIG. 42, clips 1008 extend into the lumen 1006 to removably engage the head 1010 and secure an orientation of the head 1010 relative to the holder 1000. FIGS. 44-46 illustrate another embodiment of holder 1020 with separated clip arms 1024 for securing a driver head 1028, FIGS. 47-49 illustrate another embodiment of holder 1030 with wide clips 1034 for securing a driver head 1038, FIGS. 50-52 illustrate another embodiment of holder 1040 with separated wide clip arms 1044 for securing a driver head 1048, FIGS. 53 and 54 illustrate another embodiment of holder 1050 with notched arms 1054 for securing a driver head 1058, FIGS. 55-57 illustrate another embodiment of holder 1060 with protuberances 1064 for securing a driver head 1068 within an inner tube 1070 and a cap 1072, and FIGS. 58-60 illustrate another embodiment of holder 1080 for securing a driver head 1088 within an inner tube 1090 and a cap 1092 and within an outer tube 1094 and a cap 1096.

All of the proceeding holders for securing and maintaining an orientation of either a threaded shaft or a driver head therein can be used similarly to the holder 200, including through being placed within inner and outer tubes similar to tubes 100, 150 and by being sterilized and deployed such that inner environments of the inner and outer tubes remain sterile until deployment to avoid contamination of the threaded shafts and/or driver heads therein.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An implant holding system, comprising:
an outer tube having a sealed first outer end and an open second outer end, the outer tube having a removable outer cap configured to selectively seal the second outer end;
an inner tube configured to be disposed within the outer tube, the inner tube having a sealed first inner end configured to engage the outer cap of the outer tube, the inner tube having an open second inner end and a removable inner cap configured to selectively seal the second inner end;
a bone anchor having a driver head and a threaded shaft extending distally from the driver head; and
a holder configured to be disposed within the inner tube and having a longitudinal axis, the holder having a receiving head configured to receive the driver head of the bone anchor, the receiving head being configured to engage the driver head of the bone anchor to prevent axial rotation about the longitudinal axis of the holder the holder having a collar extending distally from the receiving head, the collar being configured to engage at least part of the threaded shaft of the bone anchor to maintain an orientation of the threaded shaft of the bone anchor relative to the longitudinal axis of the holder when the bone anchor is received therein, the receiving head having a lumen extending distally through the receiving head and the collar such that the threaded shaft of the bone anchor can pass therethrough.

2. The system of claim 1, wherein the holder further comprises a break-off tab removably disposed at an end opposite the receiving head, wherein the break-off tab is configured to be removed to change a length of the holder along the longitudinal axis of the holder.

3. The system of claim 1, wherein the holder has at least two bowed, deformable legs configured to maintain a position of the holder within the inner tube through a frictional engagement between each of the legs and an inner surface of the inner tube.

4. The system of claim 1, wherein the holder has an alignment panel disposed along a distal portion thereof, and the alignment panel is configured to engage an inner surface of the inner tube to resist axial rotation of the holder about the longitudinal axis of the holder.

5. The system of claim 4, wherein the alignment panel has a non-circular cross section at a point along the longitudinal axis of the holder.

6. The system of claim 1, wherein the holder, the outer tube, and the inner tube are configured to allow visualization of the orientation of the threaded shaft of the bone anchor when the bone anchor is received in the holder.

7. The system of claim 1, wherein the outer tube, the inner tube, and the holder are configured to be coaxial with each other along the longitudinal axis of the holder when the holder is disposed within the inner tube and the inner tube is disposed within the outer tube.

8. An implant holding system, comprising:
an outer tube having a sealed first outer end and an open second outer end, the outer tube having a removable outer cap configured to selectively seal the second outer end;
an inner tube configured to be disposed within the outer tube, the inner tube having a sealed first inner end configured to engage the outer cap of the outer tube, the inner tube having an open second inner end and a removable inner cap configured to selectively seal the second inner end;

a bone anchor having a driver head; and a holder configured to be disposed within the inner tube, the holder having a longitudinal axis extending between a first holder end configured to engage the inner cap of the inner tube and an open second holder end, and a lumen extending at least partially therethrough from the second holder end towards the first holder end, wherein the lumen is configured to receive at least part of the bone anchor therein, and wherein a plurality of alignment members extend at least partially into the lumen, the plurality of alignment members being configured to engage the bone anchor to maintain an orientation of the bone anchor relative to the longitudinal axis of the holder when the bone anchor is received in the lumen.

9. The system of claim 8, wherein each of the plurality of alignment members is one of a longitudinal rectangular protrusion, a perpendicular protrusion, a bowed arm, a curved arm, a spiraled arm, and a flexible arm such that a plurality of bone anchors of different lengths and diameters are receivable in the lumen.

10. The system of claim 8, wherein the holder has one or more break-off portions extending from the open second holder end toward the first holder end configured to be removed to change a length of the holder along the longitudinal axis of the holder.

11. The system of claim 8, wherein the bone anchor has a threaded shaft extending distally from the driver head, and the plurality of alignment members are arranged extending radially into the lumen to correspond with threads extending radially outward from the threaded shaft.

12. The system of claim 8, wherein the holder is configured to maintain a rotational position with the inner cap of the inner tube relative to the longitudinal axis of the holder when the holder is engaged thereto.

13. The system of claim 12, wherein the first holder end has a non-circular cross section at a point along the longitudinal axis of the holder.

14. The system of claim 8, wherein the holder, the outer tube, and the inner tube are configured to allow visualization of the orientation of the bone anchor when the bone anchor is received in the holder.

15. The system of claim 8, wherein the outer tube, the inner tube, and the holder are configured to be coaxial with each other along the longitudinal axis of the holder when the holder is disposed within the inner tube and the inner tube is disposed within the outer tube.

16. A surgical method, comprising:

removing a sealed cover from an outer tube, wherein the outer tube houses an inner tube and an implant holder is disposed within the inner tube and a threaded shaft of a bone anchor is held in a first orientation within the implant holder relative to a longitudinal axis of the implant holder through engagement with a receiving head and a collar of the implant holder, wherein an interior of the outer tube, the inner tube, the implant holder, and the bone anchor are sterile;

passing the inner tube into a sterile field without contaminating an exterior surface of the inner tube;

removing a cover from the inner tube within the sterile field; and retrieving the bone anchor from the implant holder in the inner tube within the sterile field, the threaded shaft of the bone anchor remaining in the first orientation during retrieval through engagement with the receiving head and the collar of the implant holder.

17. The method of claim 16, further comprising visually inspecting an orientation of the bone anchor through the outer tube, the inner tube, and the implant holder during removing the sealed cover from the outer tube.

18. The method of claim 16, wherein a driver head of the bone anchor engages a proximal end of the threaded shaft, and the driver head and the threaded shaft of the bone anchor are maintained in the first orientation during removing the sealed cover from the outer tube, passing the inner tube into the sterile field, and removing the cover from the inner tube.

19. The method of claim 16, wherein the implant holder is configured to hold a plurality of bone anchors of various lengths and diameters in the first orientation.

* * * * *